(12) United States Patent
Wada et al.

(10) Patent No.: US 6,172,030 B1
(45) Date of Patent: Jan. 9, 2001

(54) DETERGENT COMPOSITION

(75) Inventors: Yasunao Wada; Miyuki Kasai; Shitsuw Shikata, all of Wakayama; Atsushi Suzumatsu, Tochigi; Kenzo Koike, Tokyo; Yuji Hatada, Tochigi; Tohru Kobayashi, Tochigi; Susumu Ito, Tochigi; Masaki Tsumadori, Wakayama, all of (JP)

(73) Assignee: Kao Corporation, Tokyo (JP)

( * ) Notice: Under 35 U.S.C. 154(b), the term of this patent shall be extended for 0 days.

(21) Appl. No.: 09/402,668

(22) PCT Filed: Apr. 9, 1998

(86) PCT No.: PCT/JP98/01613

§ 371 Date: Oct. 8, 1999

§ 102(e) Date: Oct. 8, 1999

(87) PCT Pub. No.: WO98/45393

PCT Pub. Date: Oct. 15, 1998

(30) Foreign Application Priority Data

Apr. 9, 1997 (JP) .................................................. 9-091142
Sep. 8, 1997 (JP) .................................................. 9-242736

(51) Int. Cl.[7] .................................................. C11D 3/386
(52) U.S. Cl. .......................... 510/392; 510/320; 510/321; 510/530; 510/226; 510/393

(58) Field of Search ................................ 510/320, 321, 510/392, 530, 391, 393, 226

(56) References Cited

U.S. PATENT DOCUMENTS

| 3,740,315 | * | 6/1973 | Li et al. ..................................... 195/2 |
| 3,968,048 | * | 7/1976 | Bolan ........................................ 252/157 |
| 4,481,355 | * | 11/1984 | Jaskowski ................................ 536/2 |
| 5,648,263 |   | 7/1997 | Schulein et al. ....................... 436/263 |

FOREIGN PATENT DOCUMENTS

| 3906124 | * | 8/1990 | (DE) . |
| 4012351A1 |  | 10/1991 | (DE) . |
| 195 09 406A1 |  | 9/1996 | (DE) . |
| 0870834 | * | 10/1998 | (EP) . |
| 59-49279 |  | 3/1984 | (JP) . |
| 6-39596 |  | 5/1994 | (JP) . |
| WO9525790 |  | 9/1995 | (WO) . |

* cited by examiner

*Primary Examiner*—Kery Fries
(74) *Attorney, Agent, or Firm*—Birch, Stewart, Kolasch & Birch, LLP

(57) ABSTRACT

Detergent compositions containing protopectinase whose optimum pH for the reaction is 7.0 or higher when protopectin or polygalacturonic acid is used as a substrate. The detergent compositions are endowed with remarkable detergency against mud soil.

23 Claims, 4 Drawing Sheets

PECTIC ACID LYASE
AMINO ACID SEQUENCE

A P T V V H E T I

5' GCACCAACAGTAGTACACGAAACAAT 3'
   G  G  G  G    T  G  G
   C  C  C  C    C  C  C
   T  T  T  T    T  T  T

PRIMER DNA SEQUENCE

PRIMER 1

AMINO TERMINAL OF PURIFIED
PECTIC ACID LYASE

V V I G A P A A

3' CAACAATAACCACGAGGACGACG 5'
   G  G  G  G  G  G
   C  C  C  C  C  C
   T  T  T  T  T  T

PRIMER 2

LYSYL ENDOPEPTIDASE-TREATED
FRAGMENT

FIG. 1

DNA SEQUENCE AND DEDUCED AMINO ACID SEQUENCE
BETWEEN PRIMER 1 AND PRIMER 2, AS WELL AS
THE LOCATIONS OF PRIMERS 3 AND 4

PRIMER 5   5' --GCGTCGACTCGCGGGAGGCGCCGACGGTTGTTC --3'
PRIMER 6   5' --GTGTATCAAGGAGAAGACCCGGCATG --3'

FIG. 3

DETERGENT COMPOSITION

This application is the national phase under 35 U.S.C. § 371 of PCT International Application No. PCT/JP98/01613 which has an International filing date of Apr. 9, 1997, which designated the United States of America.

TECHNICAL FIELD

The present invention relates to a detergent composition, and, more particularly, to a detergent composition having excellent detergency against muddy soil.

BACKGROUND ART

Soil adhering to clothes is generally classified into organic soil and inorganic soil. Muddy soil is a typical inorganic soil. Muddy soil very commonly adheres to, for example, socks, and has been known as one of the most difficult soils to remove. Surfactants and builders, which are active components of a detergent for clothes, have relatively weak effects against inorganic soil. Therefore, a variety of technologies have been developed to enhance wash-off effect against inorganic soil. However, most of them are applied technologies making use of conventional detergent bases and have respective drawbacks. For example, carboxylic acid-based polymers such as carboxymethyl cellulose or polyacrylate, having the effect of dispersing mud therein, are difficult to incorporate in a sufficient amount due to cost and biodegradability. Use of reducing agents have also been proposed; however, it still has a problem upon incorporation because reducing agents may sometimes cause decoloration of dyed clothes.

Besides the application of the aforementioned conventional substances, there have been made attempts to use an enzyme to enhance washing effect against inorganic soil. Since an enzyme acts exclusively on a specific substrate, it exerts effects at a small amount of incorporation. Thus, an enzyme is an excellent detergent base and is expected to play more significant roles in detergent compositions. Japanese Patent Application Laid-Open (kokai) No. 59-49279 discloses that incorporation of cellulase into a detergent increases washing power against mud. Also, PCT Kohyo Publication No. 3-504080 discloses a certain cellulase which reduces harshness of cotton-containing fabrics and has effect of removing soil. Furthermore, WO95/25790 and Japanese Patent Publication (kokoku) No. 6-39596 disclose a detergent containing pectinase. Particularly, Japanese Patent Publication (kokoku) No. 6-39596 discloses that pectinase is effective against muddy soil. However, pectinase disclosed in these patent publications exhibits insufficient washing effect even when washing is conducted after presoaking at 40° C. for one hour.

In view of the foregoing, an object of the present invention is to provide a detergent composition having excellent detergency against muddy soil.

DISCLOSURE OF THE INVENTION

The present inventors have found that as compared to the case of conventional detergents, there can be obtained particularly excellent detergency against muddy soil through incorporation of protopectinase having an optimum pH for the reaction in the alkaline region, thus leading to completion of the present invention.

Accordingly, the present invention provides a detergent composition comprising protopectinase having an optimum reaction pH of 7.0 or higher when protopectin or polygalacturonic acid is used as a substrate.

BRIEF DESCRIPTION OF THE DRAWINGS

FIG. 1 shows the DNA sequences of primer 1 (SEQ ID NOS: 586) and primer 2 (SEQ ID NOS: 718) for cloning the gene for pectic acid lyase.

FIG. 3 shows primer 5 (SEQ ID NO: 13) and primer 6 (SEQ ID NO: 14) which are used for amplifying the entire area of the pectic acid lyase of the present invention. These are primers for PCR amplification described in Example 5, and the resultant amplified fragments (about 1 kbp) are digested with Sal I and subsequently ligated to pHSP64 digested with Sal I and Sma I.

Amp: Ampicillin-resistant marker gene

Tet: Tetracycline-resistant marker gene

BEST-MODE FOR CARRYING OUT THE INVENTION

Figure 2:
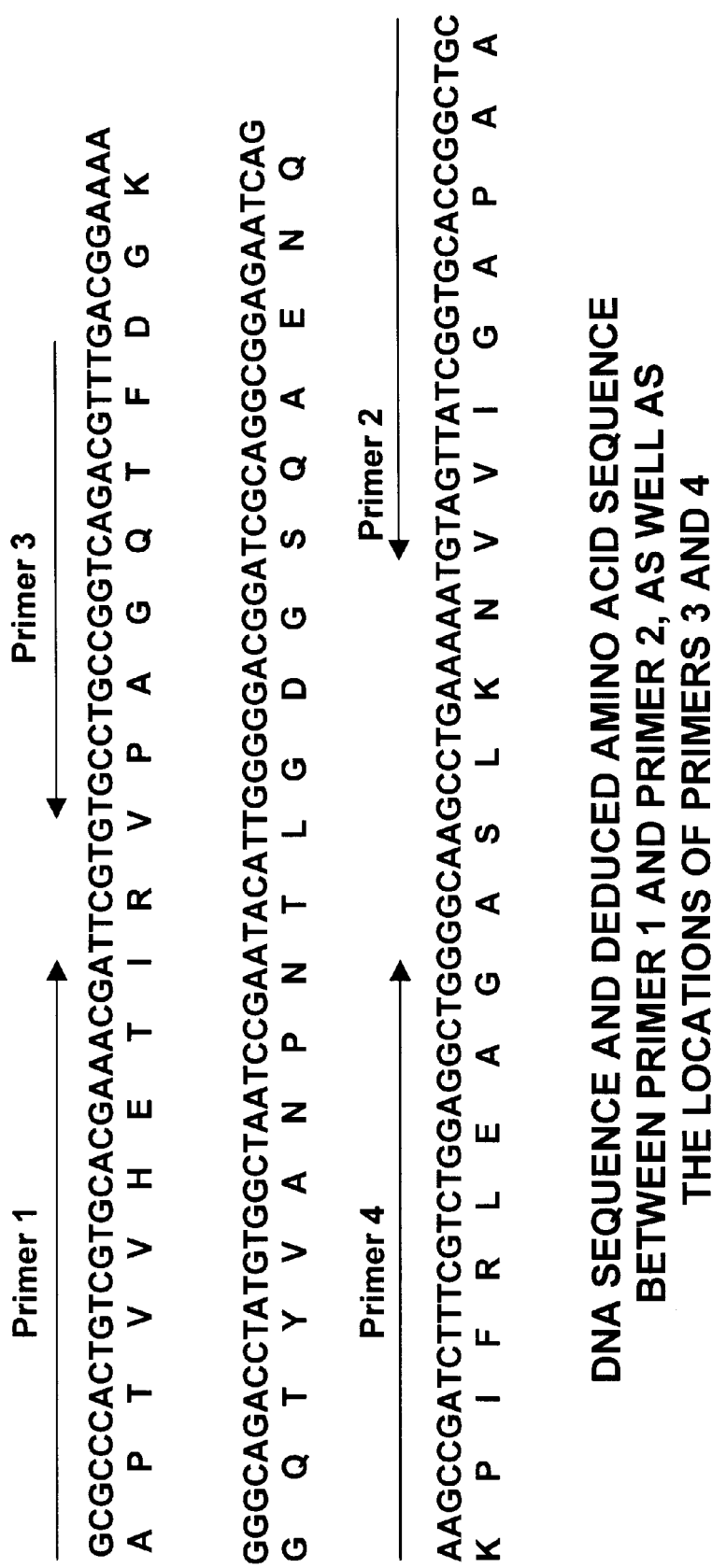
FIG. 2 shows the DNA sequence (SEQ ID NO: 9) and a deduced amino acid sequence (SEQ ID NO: 10) between primer 1 and primer 2, as well as the locations of primer 3 and primer 4. (Reverse Sequences—SEQ ID NOS: 11 & 12).

In the present invention, the term protopectinase refers collectively to enzymes acting on protopectin (insoluble natural pectin), which is a pectic substance insolubilized through mutual linkage of pectin molecules via $Ca^{2+}$, $Mg^{2+}$, or intermolecular bonding; linkage to a cellulose molecule; etc.

According to "Iwanami Seibutsugaku Jiten" (the 3rd edition, Iwanami Shoten, published on Mar. 10, 1983) and "Oyou Kosogaku (Applied Enzymology)" (edited by Yoshio Tsujisaka, p. 50, Kodansha Co., Ltd., published on Jun. 1, 1979), although the existence of protopectinase had been predicted, it had not been extracted as a sample until recently. In fact, reports on actual enzyme samples of protopectinase are quite limited (T. Sakai and M. Okushima, *Agric. Biol. Chem.*, 42, 2427, (1978); T. Sakai and M. Okushima, *Agric. Biol. Chem.*, 46, 667, (1982); T. Sakai and T. Sakamoto, *Agric. Biol. Chem.*, 54, 879, (1990); etc.).

As regards applications of protopectinase, only Japanese Patent Application Laid-Open (kokai) No. 6-220772 and "Sensyoku Kogyo (Dye Industries)" (Vol. 43, No. 4, p. 162–173 (1995) describe its use in scouring of fibers. So far there exist no published reports that disclose incorporation of protopectinase into a detergent composition.

Protopectinase is known to be classified into two types; type A and type B (Sakai, Sakamoto, "Sen-i Kogaku (Fiber Engineering)," 45, 301 (1992)). The type A protopectinase decomposes a polygalacturonic acid moiety in protopectin for solubilization, and the type B protopectinase acts on the remaining moieties (e.g., linkage site between a pectic substance and a cellulose molecule). Both types of protopectinase; i.e, types A and B, may be used in the present invention.

The protopectinase used in the present invention has an optimum pH for the reaction of 7.0 or higher in a reaction system in which protopectin or polygalacturonic acid serves as a substrate. From the point of detergency, the optimum pH for the reaction is preferably 7.5 or higher, more preferably 8.0 or higher. The optimum pH for the reaction can be measured in a variety of buffer systems known to those skilled in the art, and the optimum pH for the reaction must be 7.0 or higher in at least one of such buffer systems. When protopectin is the substrate, cotton fibers containing a pectic substance are used, and for measurement purposes, those having a high pectic substance content are preferred. When protopectinase is of type A and has pectinase activity, the optimum pH for the reaction may be obtained through use of, for example, pectic acid as a substrate. As will be described in the Examples section hereinbelow, a system for measuring an optimum pH for the reaction may include Britton-Robinson universal buffer (phosphoric acid/acetic acid/boric acid/sodium hydroxide) ("Shin Jikkenkagaku-koza 20," Biochemistry [II], edited by The Chemical Society of Japan, p. 1229, Maruzen K. K., published on Oct. 20, 1978) or glycine-NaOH buffer and, as a substrate, cotton fabric or polygalacturonic acid.

Protopectinase which is used in the present invention preferably has high ability to release cotton-derived pectin at pH 8.0. In consideration of washing effects, ability to release cotton-derived pectin in an amount of 0.2 mg/g-cotton is more preferred. As used herein, ability to release cotton-derived pectin is defined as an amount of pectin released from cotton yarn (1 g) after the enzyme (0.4 mg/ml) is allowed to react with cotton yarn (20 mg/ml) at 30° C. for one hour, and is measured by a method shown in detail in the below-described Examples.

No particular limitation is imposed on the source of the protopectinase of the present invention, and enzymes found in a wide range of plants, bacteria, and fungi may be used. Examples include a bacterium such as Bacillus; a yeast such as Tricosporon, Endomyces, Endomycopsis, Saccharomyces, Schizosaccharomyces, Pichia, Hansenula, Debaryomyces, Hanseniaspora, Torulopsis, Candida, or Kluyveromyces; and a mold such as Fusarium, Galactomyces, Aspergillus, Rhizopus, or Trametes. Of these, Bacillus-derived protopectinase is particularly preferred.

Protopectinase used in the present invention may also exhibit another enzyme activity, so long as it exhibits the above-described protopectinase activity. For example, pectic acid lyase exhibiting protopectinase activity may be used.

Examples of enzymes exhibiting protopectinase activity include pectic acid lyase produced by Bacillus sp. KSM-P15 or Bacillus sp. KSM-366; type B protopectinase derived from Bacillus Subtilis IFO12113; an enzyme having an amino acid sequence with one or more amino acids being deleted, replaced, or added; and an enzyme being immunoreactive with an antibody of these enzymes.

An enzyme derived from strain KSM-P15 is particularly preferred in the present invention. The amino acid sequence of the pectic acid lyase exhibiting protopectinase activity produced by strain KSM-P15 is shown in Sequence No. 1. In the present invention, there may be used an enzyme having an amino acid sequence of Sequence No. 1 or an amino acid sequence of Sequence No. 1 with one or more amino acids being deleted, replaced, or added. No particular limitation is imposed on the deletion, replacement, or addition (hereinafter may be referred to as mutation) so long as the protopectinase and pectic acid lyase are not deactivated, and the mutation preferably conserves lysine at the 107th position, lysine at the 129th position, and arginine at the 132nd position in Sequence No. 1. Also, the degree of mutation is not particularly limited so long as the above-described 107th position, 129th position, and 132nd position are conserved. Preferably, 55.7% or higher homology exists between amino acid Nos. 36 and 132 of Sequence No. 1. More preferably, the homology is 70% or higher, particularly preferably 80% or higher.

The following is a more detailed description of enzymological characteristics of the pectic acid lyase exhibiting protopectinase activity produced from Bacillus sp. KSM-366 strain. The measurement thereof is described hereinlater (see Example III-1-B).

(1) Action
To cleave α-1,4-bond of pectic acid (polygalacturonic acid) via β-elimination in an endo fashion and to provide a double bond at the C4–C5 position of the non-reduced end to form unsaturated digalacturonide or unsaturated oligo-galacturonide.

(2) Substrate specificity
To act on protopectin, pectic acid (polygalacturonic acid), acid-soluble pectic acid, and pectin.

(3) Optimum pH
pH 8.0–9.0 (Britton-Robinson universal buffer)

(4) Optimum temperature
approximately 60° C. (pH 8, Tris-HCl buffer)

(5) Molecular mass
approximately 43 kDa (as measured by SDS-PAGE)

(6) Isoelectric point
approximately pH 10.3 (isoelectric focusing PAGE)

The following is a more detailed description of enzymological characteristics of the pectic acid lyase exhibiting protopectinase activity produced by Bacillus sp. KSM-P15 strain. The measurement thereof is described below (see Example III-2-B).

(1) Action
To cleave α-1,4-bond of pectic acid (polygalacturonic acid) via β-elimination in an endo fashion and to provide a double bond at the C4–C5 position of the non-reduced end to form unsaturated digalacturonide or unsaturated oligo-galacturonide.

(2) Substrate specificity
To act on protopectin, pectic acid (polygalacturonic acid), acid-soluble (3) Optimum pH pectic acid, and pectin.

(3) Optimum pH
pH 10.3–10.7 (glycine-NaOH buffer)

(4) Optimum temperature
50–55° C. (pH 10.5, glycine-NaOH buffer)

(5) Molecular mass
approximately 20–21 kDa (as measured by sedimentation equilibrium; approximately 26 kDa as measured by SDS-PAGE)

(6) Isoelectric point
approximately pH 10.3 (isoelectric focusing PAGE)

(7) Amino acid terminal sequence
including APTVVHETIRVPAGQTFDGK (SEQ ID NO: 3)

Each of the above enzymatic values contains values for variant strains. As far as KSM-P15 strains are concerned, optimum temperature is 50–55° C., molecular mass is about 20–21 kDa, and isoelectric point is about pH 10.3.

Examples of the microorganism producing the above-described enzyme exhibiting protopectinase activity include the above-described microorganisms; variants thereof; and host cells transformed by recombinant DNA having a DNA sequence coding for these enzymes and mutants thereof.

In order to create a recombinant vector, the gene is inserted into an arbitrary vector which is suitable for expression of the gene in a host of interest. Examples of the vector include pBR 322, pUC18, and pUC19 for cases in which *Escherichia coli* is used as the host, and pUB110 for cases in which *Bacillus subtilis* is used as the host.

In order to produce the enzyme exhibiting protopectinase activity by use of the aforementioned microorganism producing an enzyme exhibiting protopectinase activity; a variant thereof; or host cells transformed by recombinant DNA having a DNA sequence coding for these enzymes and mutants thereof, the microorganism strain may be inoculated to a culture medium containing an assimilatory carbon source, nitrogen source, and other essential nutrients and then incubated by a general method.

The target substance; i.e., an enzyme exhibiting protopectinase activity, may be collected from the thus-obtained culture broth and purified through general methods for collection and purification of enzymes. The thus-obtained enzyme solution may be used without any further treatment or may further be purified, crystallized, or granulated through known methods. When the enzyme solution is used in a detergent composition, the culture broth may be concentrated, dialyzed, and then spray-dried to obtain granules through known methods.

No particular limitation is imposed on the amount of protopectinase incorporated in the detergent composition of the present invention so long as the enzyme activity is satisfactorily expressed, and the above-mentioned releasability for cotton pectin may serve as an index of the preferable incorporation amount. For example, the protopectinase is incorporated into a washing solution in an amount of 0.001–500 mg/L, more preferably 0.05–50 mg/L reduced as the amount of the enzyme sample, so that the above-mentioned releasability for cotton pectin may be 0.2 mg/g-cotton or more. When the protopectinase of the present invention belongs to A type and exhibits pectinase activity, the enzyme may be incorporated in an amount of 1–10,000 U/L, more preferably 5–5,000 U/L, particularly preferably 10–2,000 U/L as the concentration at the washing determined by the below-described measuring method for protopectinase activity.

In order to obtain a high washing effect against muddy smear, it is important to employ an enzyme exhibiting protopectinase activity in an alkaline region in which actual washing is conducted. Specifically, it is preferred that protopectinase having an optimum reaction pH of 7.0 or higher or protopectinase having a releasability for cotton pectin of 0.2 mg/g-cotton or more at the pH of 8.0 be incorporated. In other words, it is important for the embodiment of the present invention that the protopectinase acts to cause release of cotton pectin in an alkaline solution containing the detergent.

Also, the detergent composition of the present invention may contain a known detergent component, examples of which include the following.

(1) Surfactant:

Examples of surfactants include anionic surfactants such as linear alkylbenzenesulfonates having a C10–C18 (average) alkyl group, alkyl ether sulfonates onto which ethylene oxide is added (average 0.5–8 mol/molecule), having a C10–C20 (average) linear or branched alkyl group, alkylsulfates having a C10–C20 (average) alkyl group, olefinsulfonates having 10–20 (average) carbon atoms in the molecule, alkanesulfonates having 10–20 (average) carbon atoms in the molecule, α-sulfo fatty acid methyl or ethyl esters having 10–20 (average) carbon atoms in the molecule, C8–C20 (average) higher fatty acid salts, alkyl ether carboxylic acids, onto which ethylene oxide is added (average 0.5–8 mol/molecule), having a C10–C20 (average) linear or branched alkyl group; nonionic surfactants such as alcohol ethoxylates having a C10–C20 (average) alkyl group and a chain of ethylene oxide units (average 1–20 mol), fatty acid alkanolamides or their alkylene oxide adducts, or ethylene oxide adducts of propylene oxide-propylene glycol condensate having a trade name of "Pluronic"; betaine-type ampholytic surfactants; sulfonate-type ampholytic surfactants; phosphate ester-type surfactants; amino acid-type surfactants; and cationic surfactants.

Of these, anionic surfactants or nonionic surfactants are preferably used as active surfactants in view of enhancing detergency. Particularly preferable examples of anionic surfactants include linear alkylbenzenesulfonates having a C10–C18 (average) alkyl group, alkylsulfonate esters, polyoxyalkylene alkyl ether sulfates, and α-sulfo fatty acid methyl esters. A tallow oil or a palm oil fatty acid salt may be added in a small amount. Preferable examples of nonionic surfactants include polyoxyalkylene (preferably oxyethylene and/or oxypropylene) alkyl ethers.

These surfactants may be incorporated in the detergent composition in an amount of 0.5–60 wt. % (hereinafter represented simply by %), particularly 10–45% for the powder detergent composition and 20–50% for the liquid detergent composition. When the detergent composition contains a bleaching agent in an amount of 40% (effective oxygen content 10% as reduced) or more, the surfactant is preferably incorporated in an amount of 1–10%, more preferably 1–5%.

(2) Other enzyme components

The detergent composition may further contain an enzyme other than protopectinase. Examples of the enzyme include hydrolases, oxidoreductases, lyases, transferases, and isomerases as classified in terms of reactivity. Of these, cellulase, protease, lipase, amylase, pullulanase, esterase, hemicellulase, peroxidase, phenol-oxidase, and pectinase other than protopectinase are particularly preferable. Commercial enzymes may be incorporated in a known amount. Examples of the preferable enzymes include protease such as protease described in Japanese Patent Application Laid-Open (kokai) No. 5-25492, Alkalase, Esperase, Savinase, Durazym (Novo Nordisk A/S), Prafect, Maxapem, or Properase (Genencor Int. Inc.); cellulase such as cellulase described in Japanese Patent Pubulication (kokoku) No. 4-43119 or Celluzyme (Novo Nordisk A/S); lipase such as Lipolase (Nova Nordisk A/S) or Lipomax (Genencor Int. Inc.); and amylase such as liquefied α-amylase described in WO94/26881, pullulanase described in Japanese Patent Publication (kokoku) Nos. 7-8993 and 7-49594, alkaline pullulanase having a-amylase activity described in Japanese Patent Application Laid-Open (kokai) No. 6-264094, Termamyl, Duramyl (Nova Nordisk A/S), Maxamyl, Prafect or OXAm (Genencor Int. Inc.).

Of these, cellulase or protease, used together with the above-described protopectinase, enhances the detergency against mud smear. Furthermore, use of cellulase and protease together with the above-described protopectinase further enhances the detergency.

(3) Bleaching agent

Addition of a bleaching agent to the detergent composition of the present invention results in further enhancement of detergency against mud smear. Examples of the bleaching agent include sodium percarbonate and sodium perborate.

(4) Metal-ion sequestering agent

Examples of sequestering agents include condensed phosphates such as tripolyphosphate, pyrophosphate, or orthophosphate; aluminosilicates such as zeolite; synthetic layered crystalline silicates; nitrilotriacetates; ethylenediaminetetraacetates; citrates; isocitrates; and polyacetal carboxylates.

Of these, crystalline aluminosilicates (synthetic zeolite) are particularly preferred. Among an A-type, an X-type, and a P-type zeolite, the A-type is preferred. The preferably used synthetic zeolite has a primary average grain size of 0.1–10 µm, particularly 0.1–5 µm.

The metal-ion sequestering agent may be added in an amount of 0–50%, preferably 5–40% and phosphorus-free metal-ion sequestering agents are preferably used.

Also preferable are crystalline silicates having high metal-ion sequestering capacity, as described in Japanese Patent Application Laid-Open (kokai) Nos. 7-89712 and 60-227895; Phys. Chem. Glasses. 7, p127–p138 (1966); Z. Kristallogr., 129, p396–p404 (1969), etc. Examples thereof include "Na-SKS-6" ($\delta$-$Na_2Si_2O_5$) commercially available from Clariant Japan Co.

(5) Anti-redeposition agent

Examples of anti-redeposition agents include polyethylene glycol, carboxylic acid polymer, polyvinyl alcohol, and polyvinylpyrrolidone. Of these, carboxylic acid polymer has metal-ion sequestering capacity and capacity for dispersing solid grain smear from clothes to a washing bath as well as anti-redeposition action. The carboxylic acid polymer includes a homopolymer or a copolymer of acrylic acid, methacrylic acid, itaconic acid, etc., and a copolymer of maleic acid and the above-described monomers is preferred. The molecular weight of the copolymer is preferably some thousands to 100,000. Also preferable is a polymer such as polyglycidic acid salt, cellulose derivative such as carboxymethyl cellulose, or aminocarboxylic acid polymer such as polyaspartic acid salt, in that these substances also have capacity for metal-ion sequestering, dispersing, and resmearing-prevention.

The anti-redeposition agent is incorporated in an amount of 0–20%, preferably 0–10%, more preferably 1–5%.

(6) Alkaline agent

Conventional alkaline agents are preferably incorporated into the detergent composition. Examples of the alkaline agents used in a powder detergent include alkali metal carbonates such as sodium carbonate generally called dense ash or light ash, and amorphous alkali metal silicates of JIS No. 1, 2, or 3. These inorganic alkaline agents are effective in forming grain cores upon drying a detergent to be able to provide a comparatively hard detergent having excellent fluidity. In place of these alkaline agents, sodium sesquicarbonate and sodium hydrogencarbonate may be used, and phosphates such as tripolyphosphates also act as an alkaline agent. Examples of the alkaline agents which may be used in a liquid detergent and act as a counter ion to a surfactant include sodium hydroxide and mono-, di-, and triethanolamine, as well as the above-described alkaline agents. The alkaline agent is preferably incorporated in the composition of the present invention in an amount of 0.01–60%, more preferably 1–50%, and particularly preferably 1–20%.

(7) As to other components, there may be incorporated conventionally known components; an extender such as sodium sulfate; a bleach-activator described in Japanese Patent Application Laid-Open (kokai) No. 6-316700 or tetraacetylethylenediamine (TAED); an enzyme-stabilizer such as boron compound or sodium sulfite; an oil-absorbing substrate such as amorphous aluminosilicate; a defoaming agent such as silicone/silica system; an anti-oxidant; a fluorescent dye; a blueing agent; and a perfume in a known amount. Specifically, components described in Japanese Patent Application Laid-Open (kokai) No. 8-218093 (p.4, 1.18+ and p.7, 1.17) may be used as the above-described components.

The detergent composition of the present invention may be manufactured through a general method using in combination the above-described protopectinase and the known components. According to use, the form of the detergent may be selected from liquids, powders, or grains. Also, the detergent composition of the present invention may be used as a detergent for clothes and a bleaching-detergent, preferably as a detergent for clothes. In the case of manufacturing a granular detergent for clothes, a separately manufactured detergent base and separately manufactured enzyme grains are preferably dry-blended to thereby obtain the detergent. Of course, the protopectinase should not be deactivated.

EXAMPLES

The present invention will next be described in detail by way of examples, which should not be construed as limiting the invention.

I. Various Measuring Methods

I-i Measurement of Optimum pH for Reaction

1) Protopectin as the substrate

An enzyme solution (0.1 ml) having an adequate concentration was added to a substrate solution (1.9 ml) containing Britton-Robinson universal buffer (pH 3 to 12) and cotton fibers (2.2% (w/v)). The mixture was allowed to incubate for 1 hour at 30° C. and then subjected to centrifugation (3000 rpm, 5 minutes, 4° C.). To the resultant supernatant (0.25 ml), chilled, concentrated sulfuric acid (96%, 3 ml) was added and mixed. A carbazole solution (0.25 ml; 0.2% carbazole/100% ethanol) was further added and mixed. The resultant mixture was allowed to develop color for 20 minutes in a 80° C. water bath and was then cooled with water for 20 minutes. Subsequently, the absorbance was measured at 525 nm. The amount of released pectin was calculated based on a calibration curve of D-galacturonic acid that was prepared simultaneously. Since cotton pectin is a protopectin, the enzyme which releases and solubilizes cotton pectin is protopectinase. The pH at which the largest amount of cotton-pectin was released was defined as the optimum pH for the reaction. Various cotton fabrics and cotton yarns may be used as cotton fibers that serve as a substrate in this measurement, but those containing a greater amount of pectic substances are preferred for the purpose of measurement, and those containing at least 5 mg of pectic substances per g of cotton as determined by the ammonium oxalate extraction method, which will be described later, are particularly preferred. Buffers other than Britton-Robinson universal buffer may be used in this measurement. Because certain buffers may affect some enzymes in their enzymatic activity, buffers known to those skilled in the art may be arbitrarily selected according to purpose and circumstances.

2) Polygalacturonic acid as the substrate

An enzyme solution (0.1 ml) having an adequate concentration was added to a substrate solution (0.9 ml) containing Britton-Robinson universal buffer (pH 3 to 12), polygalacturonic acid (PG; ICN Biomedicals, Ohio; 0.56%) and calcium chloride (0.56 mM). The mixture was allowed to incubate for 20 minutes at 30° C. To the resultant mixture, there was added 1 ml of a DNS solution (0.5% 3,5-dinitro salicylic acid; 1.61 sodium hydroxide; 30% potassium sodium tartrate). The mixture was boiled for 5 minutes so as to develop the color of reducing sugar. Immediately after the color development, the mixture was cooled with ice for approximately 15 minutes, mixed with 4 ml of ion-exchanged water, and then subjected to centrifugation (3,000 rpm, 10 minutes). Absorbance of the resultant supernatant was measured at 535 nm. The amount of produced reducing sugar was calculated based on a calibration curve of D-galacturonic acid that was prepared simultaneously. The pH at which activity was the highest was defined as the optimum pH for the reaction. Buffers other than Britton-Robinson universal buffer may be used in this measurement.

Because certain buffers may affect some enzymes in their enzymatic activity, buffers known to those skilled in the art may be arbitrarily selected according to purpose and circumstances.

I-2 Measurement of Cotton-Pectin-Release Power (pH 8.0)

An enzyme solution (0.1 ml) was added to a substrate solution (1.9 ml) containing Tris-HCl buffer (pH 8.0, 55.6 mM) and cotton fibers (2.2% (w/v)). The final concentration of enzyme in the reaction mixture was 0.4 mg/ml. The mixture was reacted for 1 hour at 30° C. and subjected to centrifugation (3,000 rpm, 5 minutes, 4° C). To the resultant supernatant (0.25 ml), chilled, concentrated sulfuric acid (3 ml, 96%) was added and mixed. A carbazole solution (0.25 ml; 0.2% carbazole/100% ethanol) was also added and mixed. The resultant mixture was allowed to develop color for 20 minutes in a 80° C. water bath and was then cooled with water for 20 minutes. Subsequently, the absorbance was measured at 525 nm. The amount of released pectin was calculated based on a calibration curve of D-galacturonic acid that was prepared simultaneously. From this, the amount of pectin released from 1 g of cotton was calculated and defined as the cotton pectin-release power at pH 8.0. Since cotton pectin is a protopectin, enzymes having cotton pectin-release power have protopectinase activity in an alkaline region. Cotton yarns that serve as a substrate in this measurement are those containing 1.5 to 2.5 mg of pectic substances per g of cotton as determined by the ammonium oxalate extraction method, which will be described later. The cotton yarns used in the present invention include sewing cotton having a yarn number count of 30 or 40 and manufactured by Kanebo Co.

I-3 Extraction of Cotton Pectin by Use of Ammonium Oxalate and Quantitative Determination of Cotton Pectin:

Pectic substances were extracted and quantitatively determined by the ammonium oxalate extraction method. Extraction operation was performed by adding finely-cut cotton to a solution of 0.5% ammonium oxalate so as to obtain a cotton concentration of 1% (w/v). The amount of extracted pectic substances was determined by the carbazole sulfate method. The method of extraction and quantitative analysis was performed according to the method described in "The Research Reports by Hamamatsu Technology Center, Shizuoka" (No. 4, p.17–22, 1994).

I-4 Determination of Pectinase Activity in Enzyme Powders

An enzyme solution (0.1 ml) having an adequate concentration was added to a substrate solution (0.9 ml) containing a buffer, polygalacturonic acid (PG; ICN Biomedicals, Ohio; 0.56%) and calcium chloride (0.56 mM). The mixture was allowed to incubate for 20 minutes at 30° C. As a buffer for a substrate solution, glycine-NaOH buffer (pH 10.0, final concentration: 50 mM) was used for determining an alkaline enzyme, while citric acid buffer (pH 5.0; final concentration: 10 mM) was used for determining an acidic enzyme. To the resultant mixture, there was added 1 ml of a DNS solution (0.5% 3,5-dinitro salicylic acid; 1.6% sodium hydroxide; 30% potassium sodium tartrate). The mixture was boiled for 5 minutes so as to develop the color of reducing sugar. Immediately after the color development, the mixture was cooled with ice for approximately 15 minutes, mixed with 4 ml of ion-exchanged water, and then subjected to centrifugation (3,000 rpm, 10 minutes). Absorbance of the resultant supernatant was measured at 535 nm. The amount of produced reducing sugar was calculated based on the calibration curve of D-galacturonic acid that was prepared simultaneously, to thereby obtain the enzymatic activity. Regarding enzymatic activity, the amount of enzyme that produced reducing sugar equivalent to 1 µmol of galacturonic acid in one minute was defined as 1 U.

I-5 Measurement of Cellulase Activity

An enzyme solution (0.1 ml) having an adequate concentration was added to a substrate solution (0.9 ml) containing carboxymethylcellulose (CMC: Sunrose AO1MC, DS=0.65 to 0.75, DP=250, Nihon Seishi Co.; 1.1%) and glycine-NaOH buffer (pH 10.0, 111 mM). The mixture was allowed to incubate for 20 minutes at 40° C. To the resultant mixture, there was added 1 ml of a DNS solution (0.5% 3,5-dinitro salicylic acid; 1.6% sodium hydroxide; 30% potassium sodium tartrate). The mixture was boiled for 5 minutes so as to develop the color of reducing sugar. Immediately after the color development, the mixture was cooled with ice for approximately 15 minutes, and then mixed with 4 ml of ion-exchanged water. Absorbance of the resultant supernatant was measured at 535 nm. The amount of produced reducing sugar was calculated based on a calibration curve of D-glucose that was prepared simultaneously, to thereby obtain the enzymatic activity. Regarding enzymatic activity, the amount of enzyme that produced reducing sugar equivalent to 1 µmol of glucose in one minute was defined as 1 U.

I-6 Measurement of Protease Activity

Degradation activity toward urea-denatured hemoglobin was determined by the moddified Anson-Hemoglobin Method (M. L. Anson, J. Gen. Physiol., 22, 79, 1938) as follows. An enzyme solution (0.1 ml) having an adequate concentration was added to a substrate solution (0.65 ml) containing urea-denatured hemoglobin (1.70%) and calcium chloride (0.46 mM) in the reaction mixture. The mixture was allowed to incubate for 20 minutes at pH 10.5 and 25° C. To the resultant mixture, there was added 1 ml of trichloroacetic acid (TCA: 5% w/v solution) so as to stop the reaction. The mixture was subjected to centrifugation (3000 rpm, 10 minutes). Protein present in the resultant supernatant was allowed to develop color by phenol reagent. The amount of TCA soluble protein was calculated based on a calibration curve of tyrosine that was prepared simultaneously, to thereby obtain the enzymatic activity. Regarding enzymatic activity, the amount of enzyme that produced TCA soluble protein equivalent to 1 mmol of tyrosine in one minute was defined as 1 U.

II. Isolation of Alkaline Protopectinase-producing Microorganisms

II-1. Isolation of Bacillus sp. KSM-366 Strain

Soils from various places in Japan and suspended in sterilized water or strains stocked in the microorganism-collection of Kao Corporation were applied on an agar plate culture medium containing polygalacturonic acid and then cultured at 30° C. for 3–5 days. When bacteria had been grown, 1% (w/v) CTAB (cetyltrimethylammonium bromide) solution was poured into the culture medium, and the resultant medium was allowed to stand for 10 minutes. Bacteria which formed clear zones around colonies due to decomposition of polygalacturonic acid were selected and preserved as a pectic-acid-lyase-producing bacterium, to thereby prepare crude enzyme that was subjected to various tests. In this manner, Bacillus sp. KSM-366 strain was selected as a bacterium producing an enzyme having alkaline protopectinase activity.

Mycological properties of the strain KSM-366 are as follows:

A Morphological properties

| | |
|---|---|
| (a) Shape and size of cell | rods (0.6–0.8) × (3–5) $\mu$m |
| (b) Polymorphism | no |
| (c) Motility | (peritrichous flagella) |
| (d) Spore (size, shape, location, swollen) | (0.6–1.0) × (1.0–5) $\mu$m, central to subterminal, not swollen |
| (e) Gram staining | positive |
| (f) Acid-fastness | negative |
| (g) Growth on meat broth agar plate | opaline, smooth or leaf-shaped colony formation |
| (h) Litmus milk | alkalization, liquefaction |

B Physiological properties

| | |
|---|---|
| (a) Reduction of nitrate | positive |
| (b) Denitrification | negative |
| (c) MR test | negative (pH 5.8) |
| (d) VP test | positive |
| (e) Indole formation | negative |
| (f) Hydrogen sulfide formation | negative |
| (g) Starch hydrolysis | positive |
| (h) Utilization of citric acid | positive (Christensen, Simmons culture medium) |
| (i) Utilization of inorganic nitrogens | utilization of nitrate and ammonium salt |
| (j) Pigment formation | no |
| (k) Urease | negative |
| (l) Oxidase | positive |
| (m) Catalase | positive |
| (n) Growth temperature range | 10° C.–45° C. (optimum temperature: 30° C.–40° C.) |
| (o) Growth pH range | pH 5–11 (optimum growth pH: pH 6–9) |
| (p) Oxygen effect on growth | growth under anaerobic conditions |
| (q) OF test | - (growth with no color change) |
| (r) Sodium chloride-fastness | growth on medium containing 10% sodium chloride |
| (s) Acid formation from sugar | acid generation from galactose, xylose, arabinose, sucrose, glucose, mannitol, mannose, inositol, sorbitol, trehalose, glycerin, maltose, fructose, raffinose, melibiose and soluble starch; no acid formation from lactose |
| (t) Gas formation from glucose | no |

A study of the above-described mycological properties based on the description in "Berger's Manual of Systematic Bacteriology" (Williams & Wilkins Co., 1984) reasonably suggested that this strain belongs to *Bacillus licheniformis*. However, the present strain is not capable of survival at a temperature over 45° C. and is capable of survival at a maximum pH of 11. Since known strains of Bacillus licheniformis do not have these properties, this strain is a novel microorganism. Consequently, we deposited this strain, a new microorganism, with the National Institute of Bioscience and Human Technology, Agency of Industrial Science and Technology as Bacillus sp. KSM-366 (FERM BP-6262).

II-2 Isolation of Bacillus sp. KSM-P15 Strain

In the same manner as described in II-1, Bacillus sp. KSM-P15 strain was isolated as a bacterium producing an enzyme exhibiting alkaline protopectinase activity.

Mycological properties of the strain KSM-P15 are as follows:

A Morphological properties

| | |
|---|---|
| (a) Shape and size of cell | rods (0.3–0.5) × (1.6–2.1) $\mu$m |
| (b) Polymorphism | no |
| (c) Motility | yes |
| (d) Spore (size, shape, location, swollen) | (0.6–0.7) × (1.2–1.4) $\mu$m, central to subterminal, swollen |
| (e) Gram staining | positive |
| (f) Acid-fastness | negative |
| (g) Growth on meat broth agar plate | yellowish white, punctiform, raised, entire colony formation |
| (h) Litmus milk | slightly red without coagulation |

B Physiological properties

| | |
|---|---|
| (a) Reduction of nitrate | positive |
| (b) Denitrification | negative |
| (c) MR test | negative (pH 5.5) |
| (d) VP test | positive |
| (e) Indole formation | negative |
| (f) Hydrogen sulfide formation | negative |
| (g) Starch hydrolysis | positive |
| (h) Utilization of citric acid | positive |
| (i) Utilization of inorganic nitrogens | no utilization of nitrate and ammonium salt |
| (j) Pigment formation | no |
| (k) Urease | negative |
| (l) Oxidase | positive |
| (m) Growth temperature range | 20° C.–45° C. |
| (n) Growth pH range | pH 7–10 |
| (o) Oxygen effect on growth | growth under anaerobic conditions |
| (p) OF test | growth, no color change |
| (q) Gas formation from glucose | no |
| (r) Sodium chloride-fastness | no growth on medium containing 3% sodium chloride |
| (s) Acid formation from sugar | acid generation from galactose, xylose, arabinose, sucrose, glucose, mannitol, mannose, trehalose, lactose, glycerin maltose, fructose raffinose, melibiose and soluble starch; no acid formation from inositol or sorbitol |

A study of the above-described mycological properties based on the description in "Berger's Manual of Systematic Bacteriology" (Williams & Wilkins Co., 1984) reasonably suggests that this strain belongs to *Bacillus circulans,* which is a strain having many variants. However, the present strain has properties which do not completely accord with those of known strains of *Bacillus circulans,* and therefore is a novel microorganism. Consequently, this strain, a new microorganism, was deposited with the National Institute of Bioscience and Human Technology, Agency of Industrial Science and Technology as Bacillus sp. KSM-P15 (FERM BP-6241).

III. Preparation of Pectic Acid Lyase having Alkaline Protopectinase Activity and Enzymological Properties Thereof III-1 Pectic Acid Lyase Produced by Bacillus sp. KSM-366 Strain A. Preparation of Enzyme Bacillus sp. KSM-366 strain was cultured in nutrient broth (0.8%) containing pectic substances (0.5%) and sodium carbonate (0.5%) for 72 hours in total. Subsequently, the culture broth was centrifugated so as to remove cells. The thus-obtained supernatant was concentrated by ultrafiltration (6,000-Mr cutoff). The resultant concentrated solution was lyophilized, to thereby obtain enzyme powders. The thus-obtained enzyme powders exhibit protopectinase activity, and will hereinafter be called Protopectinase A.

Subsequently, Protopectinase A was dissolved in 25 mM Tris-HCl buffer (pH 7.5), and applied to a column (5×20 cm) of Super Q Toyopearl 650C (product of Toso Co.) equilibrated with the same buffer. The proteins eluted with the equilibration buffer (proteins which were not adsorbed by the column) were collected and then loaded to a column (2.5×20 cm) of SP Toyopearl 550C (product of Toso Co.) equilibrated with 20 mM phosphoric acid buffer (pH 6.0). The column was washed with the equilibration buffer and proteins were eluted with a linear gradient of 0–0.3 M sodium chloride in the equilibration buffer to thereby collect proteins exhibiting pectinase activity. The thus-obtained fractions were concentrated by ultrafiltration (PM10 Diaflo membrane, product of Amicon; 10,000-Mr cutoff), subsequently applied to a column (2.6×60 cm) of Sephacryl S-200 (product of Pharmacia) equilibrated with 50 mM Tris-HCl buffer (pH 7.5) containing 100 mM sodium chloride and 1 mM calcium chloride, and then eluted with the buffer. The pectinase activity fractions comprising almost a single protein, were collected and dialyzed, and then lyophilized, to thereby obtain purified enzyme powder. The thus-obtained enzyme exhibits protpectinase activity and will be called Protopectinase PA.

B. Enzymological Properties (a) Standard Enzymatic Activity

The substrate solution (3 ml) containing 0.1 M Tris-HCl buffer (pH 8), 0.5 mM calcium chloride, and 0.2% polygalacturonic acid (manufactured by Sigma) was incubated at 30° C. for 5 minutes. An appropriately diluted enzyme solution [0.1 ml, diluted with 50 mM Tris-HCl buffer containing 1 mM calcium chloride (pH 7.5)] was added to initiate reaction. The mixture was incubate at 30° C. for 20 minutes and then allowed to stand for 5 minutes in boiling water to terminate the enzymatic reaction. The quantity of unsaturated oligogalacturonic acid formed in the reaction was determined through measuring the absorbance at 235 nm and calculating with the molar extinction coefficient of unsaturated digalacturonide (4600 $M^{-1}$ $cm^{-1}$, Hasegawa & Nagel, *J. Food Sci.*, 31, 838–845, 1966). There was used a test blank that was allowed to stand for 5 minutes in boiling water immediately after the addition of the enzyme solution. One unit of enzyme (1U) is defined as the amount of enzyme that produces unsaturated oligogalacturonic acid equivalent to 1 µmol of unsaturated digalacturonide per minute under the above-described reaction conditions. In the experiment to determine the optimum pH for the reaction, the time scan method was employed to directly determine the increase in absorbance at 235 nm.

(b) Optimum pH

The optimum pH for the reaction was investigated by the standard enzymatic activity measuring method through use of 0.2 M Britton-Robinson universal buffer (pH 6.5–12.0). The results show that the optimum pH for the reaction is 8.0–9.0.

(c) Optimum Temperature

The optimum temperature for the reaction was investigated through use of 0.1 M Tris-HCl buffer (pH 8.0) at temperatures between 5° C. and 70° C. inclusive. The results show that the enzyme acts in a wide temperature range of 10° C.–70° C., with approximately 60° C. being optimum.

(d) Molecular Mass

The molecular mass of the enzyme was estimated to be approximately 43 kDa by SDS-PAGE (12.5% gel).

(e) Isoelectric Point

The isoelectric point of the enzyme was determined to be approximately pH 10.3 by the isoelectric focusing PAGE by use of 5% polyacrylamide gel containing an ampholyte of pH 8–10.5 or pH 3–10 (Pharmalyte, product of Pharmacia).

III-2. Pectic Acid Lyase Produced by Bacillus sp. KSM-P15 Strain

A. Preparation of Enzyme

In the same manner as described in III-1 A, Bacillus sp. KSM-P15 strain was cultured, and the enzyme powders were prepared. The obtained enzyme powders exhibit protopectinase activity, and will hereinafter be called Protopectinase B.

Subsequently, Protopectinase B was dissolved in 50 mM Tris-HCl buffer (pH 7.5), and applied to a column (5×20 cm) of Super Q Toyopearl 650C (product of Toso Co.) equilibrated with the same buffer. The proteins eluted with the equilibration buffer (proteins which were not adsorbed by the column) were collected and then injected to a Bio Cad60 HPLC system (product of Nihon Perceptive Co.) equipped with a HS column (sulphopropyl group; 1×10 cm) equilibrated with 20 mM Tris-HCl buffer containing 0.2 mM calcium chloride (pH 7.0). Protein adsorbed onto the column was eluted with a linear gradient of 0–0.2 M sodium chloride in the equilibration buffer, to thereby collect fractions exhibiting pectinase activity and comprising almost a single protein. The thus-obtained fractions were dialyzed and lyophilized, to thereby obtain a purified enzyme powder. The resultant enzyme exhibits protpectinase activity and will be called Protopectinase PB.

B. Enzymological Properties (a) Standard Enzymatic Activity 0.5 M glycine-NaOH buffer (pH 10.5) (0.3 ml), 6 mM calcium chloride (0.3 ml), and ion-exchanged water (1.7 ml) were placed in a test tube, which was then incubated at 30° C. for 5 minutes. An appropriately diluted enzyme solution [0.1 ml, diluted with 50 mM Tris-HCl buffer containing 1 mM calcium chloride (pH 7.5)] was added to the test tube, which was further incubated at constant temperature for 5 minutes. An aqueous solution of polygalacturonic acid (0.6 ml, 1% (w/v), product of ICN Biochemicals Co.) was added to the enzyme solution to initiate reaction, and the mixture was incubated at 30° C. for 10 minutes. The reaction was terminated by the addition of 3 ml of 50 mM HCl. The quantity of unsaturated oligogalacturonic acid formed in the reaction was determined through measuring the absorbance at 235 nm and calculating with the molar extinction coefficient of unsaturated digalacturonide (4,600 $M^{-1}$ $cm^{-1}$, S. Hasegawa and C. W. Nagel, *J. Food Sci.*, 31, 838–845, 1966). A test blank was prepared as follows: 50 mM hydrochloric acid (3 ml) was added to a reaction mixture treated without being incorporated with the enzyme solution, and subsequently an enzyme solution (0.1 ml) was added thereto. One unit of enzyme (1 U) is defined as the amount of enzyme that produces unsaturated oligogalacturonide equivalent to 1 μmol of unsaturated digalacturonide per minute under the above-described reaction conditions.

(b) Optimum pH

The optimum pH for the reaction was investigated by the standard enzymatic activity measuring method employing 50 mM Tris-HCl buffer (pH 7–9) or 50 mM glycine-NaOH buffer (pH 8.5–11.0). The enzyme exhibits the highest rate of reaction in glycine-NaOH buffer (pH 10.5). At pH 10.3–10.7, the activity is 90% or more of the maximum activity, and the activity is 70% or more of the maximum activity between pH 10 and 11.

(c) Optimum Temperature

The optimum temperature for the reaction was investigated through use of 50 mM glycine-NaOH buffer (pH 10.5) at temperatures between 10° C. and 70° C. inclusive. The results show that the enzyme acts in a wide temperature range of 10° C.–65° C., with 50–55° C. being optimum.

(d) Molecular Mass (d-1) The molecular mass of the enzyme obtained through sedimentation equilibrium experiment is 20.3±1.0 kDa.

(d-2) The molecular mass of the enzyme was estimated to be approximately 26 kDa by SDS-PAGE (15% gel). A molecular weight marker (SDS-PAGE Molecular Weight Standards, Low Range, Product of Bio-Rad) was used as a standard protein.

(e) Isoelectric Point

The isoelectric point of the enzyme was determined to be approximately pH 10.3 by the isoelectric focusing PAGE by use of 5% polyacrylamide gel containing an ampholyte of the pH 8–10.5 (Pharmalyte, product of Pharmacia).

(f) Amino Acid Terminal Sequence

The enzyme was blotted on a ProSorb filter (Perkin-Elmer Co.) and was analyzed by use of a protein sequencer (model 674, Applied Biosystem Co.), to determine the amino acid sequence up to the 20th amino acid; i.e., APTVVHE-TIRVPAGQTFDGK.

(g) Internal Amino Acid Sequence

The enzyme was treated with lysyl endopeptidase. The internal peptides were fractionated from the treated solution by use of an automated C-terminal fragment fractionator (CTFF-1: Shimadzu Co.). The sample was blotted on a ProSorb filter and the N-terminal amino acid sequence was determined by use of a protein sequencer to thereby obtain the sequence of VVIGAPAADGVH (SEQ ID NO: 4).

(h) Effects of Chemical Reagents

Various chemical reagents were added to 50 mM Tris-HCl buffer (pH 7.5). An enzyme solution was added thereto. After the mixture was incubated at 30° C. for 1 hour, the residual activity was measured through the standard conditions of assay. The results show that the enzyme is not inhibited by surfactants (0.01–0.1%), chelating agents (0.15–0.20%), or other compounds.

IV. Cloning of the Gene for Pectic Acid Lyase Derived from Bacillus sp. KSM-P15 Strain and Preparation of the Corresponding Enzyme from Transformants IV-1. Cloning of the Gene A. Preparation of Genomic DNA Bacillus sp. KSM-P15 strain was cultured aerobically in a liquid culture medium with shaking, and the culture broth was centrifuged to collect cells. The genomic DNA was prepared from the obtained cells according to Saito and Miura (Biochim. Biophys. Acta, 72, 619–629, 1963).

B. Preparation of Primers

Primer 1 and primer 2 were synthesized based on the results of Example B-f and Example B-g in (III-2) (FIG. 1).

C. Cloning

PCR was conducted by use of primer 1 and primer 2, and genomic DNA (0.5 μg) of Bacillus sp. KSM-P15 as a template. The obtained amplified fragment was purified with a PCR fragment purification kit (Boehringer Mannheim) and cloned by introducing the fragment to the Sma I site of a plasmid vector pUC19. A partial gene sequence of the target pectic acid lyase was detected In the determined nucleotide sequence of several obtained clones and the amino acid sequence was also deduced (See FIG. 2).

Subsequently, inverse PCR was conducted in order to amplify an upstream region and a downstream region of the above-described PCR-amplified fragment. The nucleotide sequences observed in FIG. 2, primer 3, and primer 4 were used. A genomic DNA (1 μg) of strain KSM-P15 was pre-digested with Pst I, extracted with phenol/chloroform, and treated with T4 DNA ligase to form an intramolecular bond (circularized DNA bond) so as to provide a template. PCR was conducted by use of a Long Template System PCR kit (TaKaRa Co.). An amplified fragment of about 2.0 kbp was detected and the DNA fragment was sequenced directly. Thus, the amino acid sequence and nucleotide sequence (SEQ ID NO: 1) of pectic acid lyase comprising 197 amino acids (SEQ ID NO: 2) from the N-terminal amino acid sequence to the amino acid before the termination codon (TAA). From the sequences, the molecular mass of the pectic acid lyase (secretion-type matured enzyme) produced from strain KSM-P15 is deduced to be 20924 Da (approximately 21 kDa).

Primer 5 (FIG. 3) was designed so as to link the deduced signal peptidase-recognizing sequence of Ala-Glu-Ala located just upstream of N-terminal amino acid, Ala, of the pectic acid lyase produced by strain KSM-P15 and the signal sequence derived from the vector employed. Primer 6 (FIG. 3) was designed to have a sequence of 26 bp located in a downstream region (by 372 bp) from the termination codon (TAA) of the gene for the pectic acid lyase.

Figure 4:
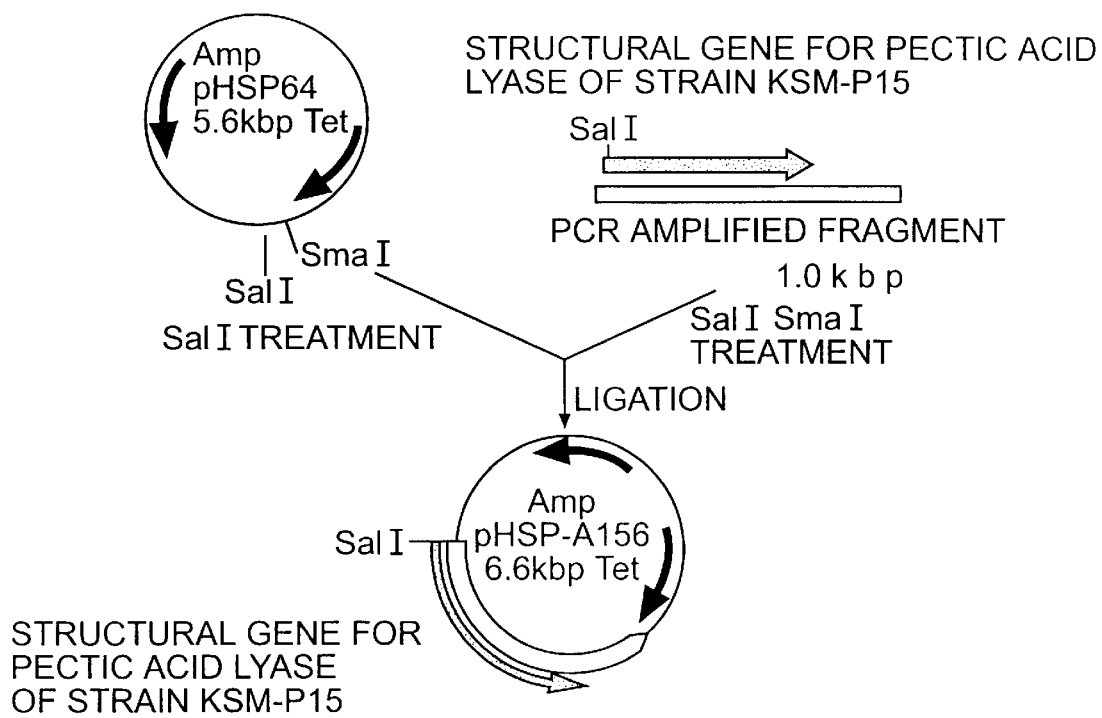
FIG. 4 shows insertion of the gene for pectic acid lyase to a vector (pHSP64), as well as the created vector for the expression of pectic acid lyase pHSP-A156.

PCR was conducted by use of primer 5 and primer 6, and genomic DNA of strain KSM-P15 as a template, to thereby amplify the DNA fragment to about 1 kbp. The DNA fragment was digested with Sal I, and ligated to pHSP64 (Sumitomo et al., Biosci. Biotech. Biochem., 56, 872, 1992) which had been-cut with Sal I and Sma I by use of a ligase (see FIG. 4).

The resultant recombinant plasmid was transformed to E. coli HB101 cells and the transformants were grown on the agar plate medium to form clear zones around colonies (See II-1 and II-2). The obtained recombinant plasmid of the present invention that codes for the gene of the present invention was named pHSP-A156.

IV-2. Preparation of the Enzyme from Transformants pHSP-A156 was introduced into Bacillus subtilis ISW1214 cells and the transformants were cultured in a liquid medium at 30° C. for three days, to thereby extracellulary produce a pectic acid lyase in a considerably large amounts.

The thus-obtained crude pectic acid lyase solution was purified in accordance with the above-described procedure III-2-A. This enzyme exhibited the propopectinase activity, and therefore, this enzyme will hereafter be called protopectinase RB. The pH vs. activity curve of protopectinase RB was almost perfectly in agreement with that of protopectinase PB.

V. Detergency Test

V-1. Preparation of Enzymes Used in the Detergency Test (a) Protopectinase A: prepared in accordance with the procedure described in III-1-A above.

(b) Protopectinase PA: prepared in accordance with the procedure described in III-1-A above.

(c) Protopectinase B: prepared in accordance with the procedure described in III-2-A above.

(d) Protopectinase PB: prepared in accordance with the procedure described in III-2-A above.

(e) Protopectinase RB: prepared in accordance with the procedure described in IV-2 above.

(f) Protopectinase C:

Protopectinase C was prepared as follows. *Bacillus subtilis* IFO 12113 was cultured in accordance with a method described by Sakai et al. (*Agric. Biol. Chem.* 53, 1213, (1989)). Subsequently, the culture broth was centrifugated so as to remove cells. The resultant supernatant was concentrated by ultrafiltration (6,000-Mr cutoff). The resultant concentrated solution was lyophilized, to thereby obtain an enzyme powder. The thus-obtained enzyme powder has ability to release cotton pectin, and therefore, this enzyme will hereafter be called Protopectinase C. Protopectinase C was determined to be classified into type B protopectinase, as it does not exhibit pectinase activity.

(g) Pectinase D:

Pectinase D was prepared as follows. Bacillus sp. KSM-S272 (National Institute of Bioscience and Human Technology, Agency of Industrial Science and Technology, Deposit No. FERM P-16066) was cultured, and the culture broth was centrifugated so as to remove cells. The resultant supernatant was concentrated by ultrafiltration (6,000-Mr cutoff). The resultant concentrated solution was lyophilized to thereby obtain an enzyme powder having pectinase activity. This enzyme will hereafter be called Pectinase D. Pectinase D exhibited alkaline pectic acid lyase activity, but did not exhibit protopectinase activity.

(h) Pectinase PD:

Subsequently, Pectinase D was dissolved in 50 mM Tris-HCl buffer (pH 7.5) containing 1 mM calcium chloride. The solution was applied to a column (2.5×10 cm) of Super Q Toyopearl 650 M (product of Tosoh Co.) equilibrated with the same buffer. The proteins eluted with the equilibration buffer (proteins which were not adsorbed onto the column) were collected and injected to a Bio Cad 60 HPLC system (product of Nihon Perceptive Co.) equipped with a HS column (sulphopropyl group; 1×10 cm) equilibrated with 20 mM Tris-HCl buffer containing 0.2 mM calcium chloride (pH 7.0). Protein adsorbed onto the column was eluted with a linear gradient of 0–0.2 M sodium chloride in the equilibration buffer, to thereby collect fractions exhibiting pectinase activity and comprising almost a single protein. The thus-obtained fractions were dialyzed and then lyophilized, to thereby obtain a purified enzyme powder. This enzyme will be called Pectinase PD. Similar to Protopectinase PA and PB, Pectinase PD exhibited alkaline pectic acid lyase activity, but did not exhibit protopectinase activity.

(i) Commercially available pectinases

The following pectinases were employed.

Sucrase N (Sankyo Co.)

Pectinase Tanabe (Tanabe Seiyaku Co.)

Pectolyase (Kikkoman Co.)

Pectinase SS (Yakult Honsha Co.)

Pectinase HL (Yakult Honsha Co.)

V-2. Activity of Enzymes Used in Detergency Test

TABLE 1

| | Optimum pH[1] | | Release of cotton pectin (pH 8.0) (mg/g fiber)[2] | Pectinase activity of enzyme powder $(\mu/g)$[3] |
|---|---|---|---|---|
| | Protopectin | Polygalacturonic acid | | |
| Present invention | | | | |
| Protopectinase A | 7~9 | 8~9 | 0.658 | 1000 |
| Protopectinase PA | 7~9 | 8~9 | 0.985 | 2500000 |
| Protopectinase B | 9 | 10.5* | 0.760 | 900 |
| Protopectinase PB | 9 | 10.5* | 1.250 | 1050000 |
| Protopectinase RB | 9 | 10.5 | 1.10 | 750000 |
| Protopectinase C[4] | 7~9 | —[5] | 0.450 | —[5] |
| Comparative enzyme products | | | | |
| Pectinase D | —[5] | 9~10 | 0.034 | 1200 |
| Pectinase PD | —[5] | 9~10 | 0.021 | 97200 |
| Sucrase N | <3 | 4~5 | 0.000 | 1580 |
| Pectinase Tanabe | <3 | 4~6 | 0.018 | 190 |
| Pectolyase | <3 | 4 | 0.031 | 3500 |
| Pectinase SS | <3 | 4 | 0.046 | 830 |
| Pectinase HL | <3 | 4 | 0.075 | 2360 |

1) Measurement was performed by use of Britton-Robinson universal buffer. The data indicated by the asterisk were obtained from the use of glycine-NaOH buffer, as measurement was not possible with Britton-Robinson universal buffer.
2) Measurement was performed by use of Tris-HCl buffer (pH 8.0).
3) For Protopectinase A, PA, B, PB, RB, and Pectinase D, activity was measured by use of glycine-NaOH buffer (pH 10.0); and for other enzymes, measurement was performed in citrate buffer (pH 5.0).
4) Type B protopectinase; does not exhibit decomposition activity toward polygalacturonic acid.
5) Unable to measure the activity (i.e., no activity).

V-3. Method for Testing Detergency

1. Test of Washing Pieces of Cloth Smudged with Muddy Soil

Pieces of cotton knitted cloth (hosiery) were smeared with Kanuma-Akadama soil (soil of the Kanuma region, Japan), to thereby prepare artificially soil-smudged pieces of cloth.

Each of the detergent compositions described hereinbelow was dissolved in 40° DH hard water (71.2 mg; $CaCO_3$/liter) so as to have a predetermined detergent concentration, to thereby prepare one liter of a detergent solution. The detergent solution was transferred to a stainless beaker for a Terg-O-Tometer. Five pieces of artificially smudged cloth were added to the detergent solution, and washed at 100 rpm and 30° C. for 10 minutes. The test pieces were rinsed with running water, iron-pressed, and then subjected to measurement of reflectance.

The reflectance of the original cloth before being smudged and that of the cloth before and after being subjected to washing were determined with an auto-recording colorimeter (Shimadzu Co.). The detergency (%) was calculated by use of the following equation.

Detergency (%)={(Reflectance after washing)−(Reflectance before washing)}/{(Reflectance of original cloth)−(Reflectance before washing)}×100

2. Washing Test for Muddy Socks

The test participants wore athletic socks (mixed fiber spinning of cotton and acrylic yarns; manufactured by Gunze Co.). Mud of the same type as that used for smudging the above-described cloth was applied to the right and left socks in even amounts. Ten socks of one group (five left socks and five right socks) were washed with a comparative detergent composition and the remaining ten socks (five right socks and five left socks) were washed with sample detergent compositions.

The manner of washing was as follows. Each detergent composition was dissolved in 30 liters of 30° C. water (40° DH) so as to have a predetermined concentration. The socks were washed in a household, two-vessel type electric washing machine for 10 minutes, rinsed with running water for 5 minutes, dewatered, and then dried.

For evaluating detergency, a pair of socks were compared with each other; while one sock washed with a reference detergent (detergent containing no enzyme) served as a control, the other sock washed with a test detergent (detergent composition containing an enzyme) was evaluated with respect to the control. Ten socks were subjectively rated by three judges, and the sum of the ratings was regarded as the ranking of evaluation for detergency. Evaluation standards were as follows.

+2: Definitely better than the reference detergent
+1: Somewhat better than the reference detergent
0: Comparable to the reference detergent
−1: Somewhat poorer than the reference detergent
−2: Definitely poorer than the reference detergent V-4: Results of Detergency Test A. Effects When the Enzymes Are Incorporated in Detergents for Clothes (a) Compositions of the Detergents Used in the Test

TABLE 2

| Ingredient (%) | Detergent (a) | Detergent (b) | Detergent (c) | Detergent (d) |
|---|---|---|---|---|
| LAS | 23.0 | | 4.0 | 20.0 |
| AS | 4.0 | 4.0 | | |
| AE-1 | 5.0 | | | |
| AE-2 | | 18.5 | | |
| AEP | | | 5.0 | |
| AES | | | 20.0 | |
| Fatty acid salt | 3.0 | 5.0 | 2.5 | 2.0 |
| Zeolite | 22.0 | 23.0 | 20.0 | |
| Amorphous aluminosilicate | | 10.0 | | |
| Sodium carbonate | 15.0 | 23.0 | | |
| Potassium carbonate | 3.0 | | | |
| Amorphous silicate | 7.0 | | | 7.0 |
| Crystalline silicate | 4.0 | 4.0 | | |
| Sodium sulfite | 2.0 | 2.0 | 0.5 | 2.0 |
| Sodium sulfate | 2.0 | 2.5 | | 23.0 |
| AA-MA | 5.0 | 5.0 | | |
| Citric acid | | | | 10.0 |
| PEG | 2.0 | 2.0 | | 2.0 |
| Monoethanolamine | | | 8.0 | |
| Ethanol | | | 5.0 | |
| Water | 3.0 | 1.0 | balance | 7.0 |
| Total | 100.0 | 100.0 | 100.0 | 100.0 |
| Shape | granular | granular | liquid | liquid |
| Concentration at use | 20 g/30 l | 20 g/30 l | 20 ml/30 l | 40 g/30 l |
| pH of washing liquid | 10.7 | 10.6 | 9.2 | 8.0 |

LAS: Sodium linear alkyl (C12–C14) benzene sulfonate (for liquid detergents, LAS of the acid type is formulated).
AS: Alkylsulfates
AE-1: Polyoxyethylene lauryl ether (average mole number of E.O. added = 4)
AE-2: Polyoxyethylene alkyl (C12 ~ C14) ether (average mole number of E.O. added = 6)
AEP: Polyoxyethylene polyoxypropylene lauryl ether (average mole number of E.O. added = 8; average mole number of P.O. added = 3)
AES: Alkylethersulfate (average mole number of E.O. added = 2.5)
Fatty acid: Palm-oil-derived fatty acid-Na
Zeolite: Type 4A zeolite, average grain size 3 μm
Amorphous amulinosilicate: See Synthesis Example 1
Sodium carbonate: Dense ash
Amorphous silicate: JIS No. 2 sodium silicate
Crystalline silicate: SKS-6 (Clariant Japan Co.), pulverized, average particle size: 15 μm.
AA-MA: Sokalan CP5, Acrylic acid - maleic acid copolymer (BASF)
PEG: Polyethylene glycol, average molecular weight 8,000

Synthesis Example 1 (Method of preparing amorphous aluminosilicate)

An aqueous solution of sodium aluminate (1,010 g; $Na_2O$ 1.55% by weight, $Al_2O_3$ 2.30% by weight, $Na_2O/Al_2O_3$= 1.11 (molar ratio)) was heated to 40° C. While the solution was stirred at 1,500 rpm, an aqueous sodium silicate solution (700 g; $Na_2O$ 2.75% by weight, $SiO_2$ 7.88% by weight, $SiO_2/Na_2O$=2.96 (molar ratio)) and calcium chloride $2H_2O$ (1.2 g) were added dropwise over 20 minutes to cause a reaction. After completion of addition, the mixture was additionally heated for a further 15 minutes. Subsequently, solid matter was collected by filtration and washed. The thus-obtained wet cake was brought to dryness at 105° C. under 300 torr for 10 hours. The dry cake was pulverized to thereby obtain a finely-divided, aluminosilicate powder, which was confirmed to be amorphous by X-ray inspection.

Atomic absorption analysis and plasma emission alanysis revealed that the thus-obtained amorphous amulinosilicate had the following composition: $Al_2O_3$ 21.1% by weight, $SiO_2$ 57.2% by weight, $Na_2O$ 20.8% by weight, and CaO 0.9% by weight ($1.65Na_2O \cdot 0.08CaO \cdot Al_2O_3 \cdot 4.75SiO_2$). The oil absorption ability was 210 ml/100 g.

(b) Test Results

Results of the tests in which washing was performed through use of detergents (a) through (d) having the compositions shown in Table 2, which were respectively added with a variety of enzymes, are described in (b-1) to (b-5) below.

As will be apparent from the results, the protopectinase-containing detergent compositions of the present invention exhibit detergency effects clearly stronger than those obtained from detergent compositions containing comparative pectinases. Moreover, when alkaline enzymes such as protopectinase A and B are incorporated, excellent effects can be exerted in detergent solutions having a high pH. Notably, such excellent effects can be obtained even when a presoaking step is omitted. It is also noted that, among pectinases that have an optimum pH for the reaction in the alkaline region, protopectinase A and B, which are capable of releasing cotton pectin, exhibit excellent detergency, whereas pectinase D, which cannot release cotton pectin, does not exhibit detergency. From this, it is concluded that alkaline protopectinase is effective as a detergent component.

(b-1) Results from the Washing Test with Detergent (a) (pH of the washing liquid: 10.7)

Washing conditions: Terg-O-Tometer 100 rpm, 10 min., 30° C.

TABLE 3

|  | Amount of enzyme added (mg/L) | Detergency against mud-smudged cloth (%) | Rating of detergency power on muddy socks |
|---|---|---|---|
| Invention Products | | | |
| Reference detergent | — | 44.3 | 0 |
| Protopectinase A | 40 | 47.7 | 30 |
| Protopectinase A | 80 | 51.5 | 44 |
| Protopectinase PA | 0.5 | 50.7 | 40 |
| Protopectinase B | 40 | 49.2 | 35 |
| Protopectinase B | 80 | 54.0 | 48 |
| Protopectinase PB | 0.5 | 53.1 | 45 |
| Protopectinase RB | 0.5 | 53.2 | 43 |
| Protopectinase C | 80 | 49.7 | 38 |
| Comparative Products | | | |
| Pectinase D | 80 | 44.8 | 5 |
| Pectinase PD | 0.5 | 43.8 | 2 |
| Sucrase N | 80 | 44.1 | 4 |
| Pectinase Tanabe | 80 | 43.8 | −2 |
| Pectolyase | 80 | 42.9 | 4 |
| Pectinase SS | 80 | 43.1 | −3 |
| Pectinase HL | 80 | 44.2 | 0 |

As is apparent from Table 3, the protopectinases of the present invention provide improved detergency even when they are incorporated in a heavy duty detergent and are used in a washing liquid of high pH. In contrast, comparative detergent compositions which contain commercially available pectinases exhibit virtually no effect. The difference in detergency between the present invention and compative products is more clear in the evaluation of detergency against muddy socks. Moreover, it is noted that, although detergency is acknowledged with crude enzyme preparations, purified enzymes provide enhanced detergency even with only small amounts of use.

(b-2) Results of a Washing Test with Detergent (b) (pH of the washing liquid: 10.6)

Washing conditions: Terg-O-Tometer 100 rpm, 10 min., 30° C.

TABLE 4

|  | Amount of enzyme added (mg/L) | Detergency against mud-smudged cloth (%) |
|---|---|---|
| Invention Products | | |
| Reference detergent | — | 43.5 |
| Protopectinase A | 40 | 46.7 |
| Protopectinase A | 80 | 51.0 |
| Protopectinase PA | 0.5 | 50.2 |
| Protopectinase B | 40 | 47.4 |
| Protopectinase B | 80 | 53.8 |
| Protopectinase PB | 0.5 | 52.7 |
| Protopectinase RB | 0.5 | 52.5 |
| Protopectinase C | 80 | 48.7 |
| Comparative Products | | |
| Pectinase D | 80 | 44.3 |
| Pectinase PD | 0.5 | 44.0 |
| Sucrase N | 80 | 44.4 |
| Pectinase Tanabe | 80 | 43.7 |
| Pectolyase | 80 | 42.6 |
| Pectinase SS | 80 | 42.9 |
| Pectinase HL | 80 | 43.5 |

As is apparent from Table 4, the protopectinases of the present invention provide improved detergency even when they are incorporated in a heavy duty detergent containing a nonionic-surfactant as a main ingredient and having a high pH of the washing liquid. In contrast, comparative detergent compositions which contain commercially available pectinases exhibit virtually no effect. It is noted that, although detergency is acknowledged with crude enzyme preparations, purified protopectinases provide enhanced detergency with only small amounts of use.

(b-3) Results of a Washing Test with Detergent (c) (pH of the washing liquid: 9.2)

Washing conditions: Terg-O-Tometer 100 rpm, 10 min., 30° C.

TABLE 5

|  | Amount of enzyme added (mg/L) | Detergency against mud-smudged cloth (%) |
|---|---|---|
| Invention Products | | |
| Reference detergent | — | 37.4 |
| Protopectinase A | 40 | 42.7 |
| Protopectinase A | 80 | 45.8 |
| Protopectinase PA | 0.5 | 44.6 |
| Protopectinase B | 40 | 42.2 |
| Protopectinase B | 80 | 45.5 |
| Protopectinase PB | 0.5 | 45.1 |
| Protopectinase RB | 0.5 | 45.3 |
| Protopectinase C | 80 | 43.6 |
| Comparative Products | | |
| Pectinase D | 80 | 38.8 |
| Pectinase PD | 0.5 | 37.1 |
| Sucrase N | 80 | 38.9 |
| Pectinase Tanabe | 80 | 38.1 |
| Pectolyase | 80 | 38.2 |
| Pectinase SS | 80 | 37.9 |
| Pectinase HL | 80 | 38.4 |

As is apparent from Table 5, it is clear that the protopectinases of the present invention provide improved detergency even when they are incorporated in a liquid detergent composition. In contrast, comparative detergent compositions which contain commercially available pectinases exhibit virtually no effect. Moreover, it is noted that, although detergency is acknowledged with crude enzyme preparations, purified protopectinases provide enhanced detergency with only small amounts of use.

(b-4) Results of a Washing Test with Detergent (d) (pH of the washing liquid: 8.0)

Washing conditions: Materials to be washed were presoaked in a 40° C. detergent solution having a concentration six times that for actual use. Subsequently, the concentration was reduced to that for actual use, and the materials were washed in a Terg-O-Tometer at 100 rpm and 30° C. for 10 min.

TABLE 6

| | Amount of enzyme added (mg/L) | Detergency against mud-smudged cloth (%) |
|---|---|---|
| Invention Products | | |
| Reference detergent | — | 42.3 |
| Protopectinase A | 40 | 46.0 |
| Protopectinase A | 80 | 48.2 |
| Protopectinase PA | 0.5 | 47.8 |
| Protopectinase B | 40 | 46.2 |
| Protopectinase B | 80 | 48.4 |
| Protopectinase PB | 0.5 | 47.7 |
| Protopectinase RB | 0.5 | 47.6 |
| Protopectinase C | 80 | 46.6 |
| Comparative Products | | |
| Pectinase D | 80 | 43.1 |
| Pectinase PD | 0.5 | 42.6 |
| Sucrase N | 80 | 44.5 |
| Pectinase Tanabe | 80 | 43.1 |
| Pectolyase | 80 | 44.8 |
| Pectinase SS | 80 | 43.7 |
| Pectinase HL | 80 | 44.2 |

As is apparent from Table 6, it is clear that the protopectinases of the present invention provide improved detergency. When presoaking was performed in a 40° C. detergent solution having a 6-fold concentration, comparative detergent compositions which contained commercially available pectinases exhibited some effect. However, the effect was far behind the effect attained by the invention products. It is noted that, although detergency is acknowledged with crude enzyme preparations, purified protopectinases provide enhanced detergency with only small amounts of use.

(b-5) Results of a Washing Test with Detergent (d) (pH of the washing liquid: 8.0)

Washing conditions: Terg-O-Tometer 100 rpm, 10 min., 30° C.

TABLE 7

| | Amount of enzyme added (mg/L) | Detergency against mud-smudged cloth (%) |
|---|---|---|
| Invention Products | | |
| Reference detergent | — | 39.4 |
| Protopectinase A | 40 | 43.0 |
| Protopectinase A | 80 | 45.4 |
| Protopectinase PA | 0.5 | 45.4 |
| Protopectinase B | 40 | 43.8 |
| Protopectinase B | 80 | 45.8 |
| Protopectinase PB | 0.5 | 44.9 |
| Protopectinase RB | 0.5 | 44.7 |
| Protopectinase C | 80 | 43.8 |
| Comparative Products | | |
| Pectinase D | 80 | 40.5 |
| Pectinase PD | 0.5 | 38.8 |
| Sucrase N | 80 | 39.9 |
| Pectinase Tanabe | 80 | 38.1 |
| Pectolyase | 80 | 40.4 |
| Pectinase sS | 80 | 39.7 |
| Pectinase HL | 80 | 41.1 |

As is apparent from Table 7, it is clear that, in the absence of presoaking, the protopectinases of the present invention provide improved detergency. In contrast, comparative detergent compositions which contain commercially available pectinases exhibit virtually no effect. Although detergency is acknowledged with crude enzyme preparations, purified enzymes provide enhanced detergency with only small amounts of use.

Furthermore, detergent compositions of the present invention were prepared by incorporating 0.1 part by weight of Protopectinase A, B, PA, PB, or RB into 100 parts by weight of the detergent compositions shown in Tables 8 and 9. When granular detergent compositions were formed, ingredients other than the enzyme, PC, AC-1, and AC-2 were first granulated to prepare a detergent base, and subsequently, the enzyme, PC, AC-1, and AC-2 were respectively granulated and blended with the detergent base granules. The thus-obtained detergent compositions have excellent detergency and are useful for washing clothes.

TABLE 8-1

| | Examples | | | | |
|---|---|---|---|---|---|
| Ingredient (%) | 1 | 2 | 3 | 4 | 5 |
| LAS-2 | 20 | | 20.5 | | 12 |
| LAS-3 | | 15 | | | |
| AS-2 | | | 5 | | 10 |
| SAS | 3 | | | | |
| AOS | | 3 | | | |
| SFE | | 8 | | | |
| Fatty acid salt | 2 | 6 | 4 | 10 | 3 |
| AES-2 | | | | | |
| AE-3 | 3 | | | | |
| AE-4 | | 3 | 3 | 15 | |
| AE-5 | | | | | |
| AG | | | | | |
| Zeolite | 30 | 18 | 15 | 15 | |
| Oil-absorbing carrier | | | | 10 | |
| Crystalline silicate | | | | 20 | |
| Amorphous silicate | 12 | 1 | 8 | | 10 |
| STPP | | | | | 25.5 |
| Sodium carbonate | 10 | 27 | 25 | 10 | 10 |
| Potassium carbonate | | 3 | | 2 | 5 |
| Sodium sulfite | 2 | 2 | | | 1 |

TABLE 8-2

(continued from Table 8-1)

| | Examples | | | | |
|---|---|---|---|---|---|
| Ingredient (%) | 1 | 2 | 3 | 4 | 5 |
| Sodium sulfate | 4.5 | 1.5 | | 1 | 11 |
| Sodium citrate | | | 4 | 2 | |
| NTA | | | | | |
| Monoethanolamine | | | | | |
| PAA | | | | | 1 |
| AA-MA | | 3 | 3 | 5 | |
| CMC | 2 | | | | |
| PEG | 5 | 2 | 2 | 2 | 2 |
| PVP | | | | | |
| Fluorescent dye | 0.3 | 0.3 | 0.3 | 0.3 | 0.3 |
| Perfume | 0.2 | 0.2 | 0.2 | 0.2 | 0.2 |
| Water | 4 | 5 | 3 | 0.5 | 6 |
| Ethanol | | | | | |
| Propylene glycol | | | | | |
| Enzyme | 2 | 2 | 2 | 3 | 3 |
| PC | | | 3 | 3 | |
| AC-1 | | | 2 | | |
| AC-2 | | | | 1 | |
| Total | 100.0 | 100.0 | 100.0 | 100.0 | 100.0 |
| Shape | granular | granular | granular | granular | granular |

TABLE 9-1

| | Examples | | | | |
|---|---|---|---|---|---|
| Ingredient (%) | 6 | 7 | 8 | 9 | 10 |
| LAS-2 | | | | 5 | 10 |
| LAS-3 | | | | | |
| AS-2 | | 20 | | | |
| SAS | | | | | |
| AOS | | | | | |
| SFE | | | | | |
| Fatty acid salt | 3 | 2 | 1.5 | | |
| AES-2 | | | 20 | | |
| AE-3 | | | | | 10 |
| AE-4 | 15 | 3 | | 15 | |
| AE-5 | | 2 | 20 | 20 | 25 |
| AG | | | | 5 | 7 |
| Zeolite | 10 | 20 | | | |
| Oil-absorptive carrier | 12 | | | | |
| Crystalline silicate | | | | | |
| Amorphous silicate | | 5 | | | |
| STPP | 20 | | | | |
| Sodium carbonate | 15 | 17.5 | 0.1 | | |
| Potassium carbonate | | | | | |
| Sodium sulfite | | | 0.2 | 0.2 | 0.2 |

TABLE 9-2

(continued from Table 9-1)

| Ingredient (%) | 6 | 7 | 8 | 9 | 10 |
|---|---|---|---|---|---|
| Sodium sulfate | 8 | 10 | | | |
| Sodium citrate | | 5 | 1.5 | 1 | 1 |
| NTA | 2 | | | | |
| Monoethanolamine | | | 4 | 5 | 6 |
| PAA | 1.5 | 3 | | | |
| AA-MA | | | | | |
| CMC | | | | | |
| PEG | | | 1.5 | | |
| PVP | | 2 | | | |
| Fluorescent dye | 0.3 | 0.3 | 0.1 | 0.1 | 0.1 |
| Perfume | 0.2 | 0.2 | 0.3 | 0.3 | 0.3 |
| Water | 1 | 5 | 43.7 | 38.2 | 30.2 |
| Ethanol | | | 5 | 5 | 5 |
| Propylene glycol | | | 2 | 5 | 5 |
| Enzyme | 2 | 2 | 0.1 | 0.2 | 0.2 |
| PC | 10 | 3 | | | |
| AC-1 | | | | | |
| AC-2 | | | | | |
| Total | 100.0 | 100.0 | 100.0 | 100.0 | 100.0 |
| Shape | granular | granular | liquid | liquid | liquid |

LAS-2: A product obtained by neutralizing alkylbenzene sulfonic acid "Alkene L" (carbon number of the alkyl chain: 10–14; product of Nisseki Senzai Co.) with 48% NaOH.
LAS-3: A product obtained by neutralizing alkylbenzene sulfonic acid "Alkene L" (carbon number of the alkyl chain: 10–14; product of Nisseki Senzai Co.) with 50% KOH.
AS-2: A sodium salt of Dovanol 25 Sulfate (C12–C15 sulfuric acid) (product of Mitsubishi Kagaku Co.).
SAS: Hostapur SAS93, (C13–C18 sodium alkane sulfonate) (product of Clariant Japan Co.).
AOS: Sodium α-olefinsulfonate
SFE: Derived from palm oil. Sodium α-sulfo fatty acid methyl ester.
Fatty acid salt: Sodium palmitate
AES-2: Polyoxyethylene alkyl (C12–C15) ether sodium sulfate (average mole number of E.O. added=2).
AE-3: Nonidet S-3 (a product obtained by adding to a C12 or C13 alcohol E.O. in an amount of three moles on average) (manufactured by Mistubishi Kagaku Co.).
AE-4: Nonidet R-7 (a product obtained by adding to a C12–C15 alcohol E.O. in an amount of 7.2 moles on average) (manufactured by Mistubishi Kagaku Co.).
AE-5: Softanol 70 (a product obtained by adding to a C12–C15 secondary alcohol E.O. in an amount of seven moles on average) (manufactured by Nippon Shokubai Co.).
AG: Alkyl(palm oil-derived)glucoside (average polymerization degree: 1.5).
Oil-absorbing carrier: Tixolex 25 (amorphous sodium aluminosilicate; manufactured by Kofran Chemical; oil absorption-ability: 235 ml/100 g).
Crystalline silicate: SKS-6; $\delta$-$Na_2Si_2O_5$; crystalline laminated silicate; average grain size: 20 $\mu$m; manufactured by Clariant Japan Co.
Amorphous silicate: JIS No.1 sodium silicate
STPP: Sodium tripolyphosphate
NTA: Sodium nitrilotriacetate
PAA: Sodium polyacrylate; average molecular weight: 12,000.
AA-MA: Sokalan CP5; acrylic acid-maleic acid copolymer.
CMC: Sunrose B1B; carboxymethylcellulose-Na; manufactured by Nihon Seishi Co.).
PEG: Polyethylene glycol; average molecular weight 6,000.
PVP: polyvinylpyrrolidone; average molecular weight 40,000; K number: 26–35.
Fluorescent dye: A 1:1 blend of Tinopal CBS (manufactured by Chiba Geigy) and Whitex SA (manufactured by Sumitomo Chemical Co.). (Note: In the case of liquid detergents, Tinopal CBS alone was incorporated.)
Perfume: Formulated in accordance with the perfume composition described in the Examples section of Japanese Patent Application Laid-Open (kokai) No. 8-239700.
Enzymes: A 2:1:1:1 blend of Savinase 12.0 TW (protease); Lipolase 100 T (lipase), Termamyl 60 T (amylase)—all these are manufactured by Novo Nordisk A/S—and KAC 500 (cellulose, manufactured by Kao Co.). (Note: In the case of liquid detergents, Savinase 16.0 L (protease; manufactured by Novo Nordisk A/S) alone was incorporated.)
PC: Sodium percarbonate; average particle size 400 $\mu$m; coated with sodium metaborate.
AC-1: TAED, tetraacetylethylene diamine; manufactured by Clariant Co., Ltd..
AC-2: Sodium lauroyloxybenzene sulfonate B. Effects when the enzymes are incorporated in bleach-detergents:

Bleach-detergents having the compositions as shown in Table 11 were prepared. Pieces of artificially mud-smudged cloth were soaked in a 0.5% aqueous solution of each detergent (20° C., 30 min.), and subsequently washed by use of a Terg-O-Tometer at 100 rpm and 20° C. for 10 minutes. The results are shown in Table 10.

TABLE 10

|  | Invention Products | | | | | | | | Comparative Products | | | |
| --- | --- | --- | --- | --- | --- | --- | --- | --- | --- | --- | --- | --- |
|  | 1 | 2 | 3 | 4 | 5 | 6 | 7 | 8 | 1 | 2 | 3 | 4 |
| Sodium percarbonate | 80.0 | 80.0 | 80.0 | 80.0 | 80.0 | 80.0 | 80.0 | 80.0 | 80.0 | 80.0 | 80.0 | 80.0 |
| Sodium carbonate (dense ash) | 16.9 | 12.9 | 16.9 | 12.9 | 16.9 | 12.9 | 16.9 | 12.9 | 17.0 | 13.0 | 17.0 | 13.0 |
| Anionic surfactant[1] | 2.0 | 2.0 | — | — | 2.0 | 2.0 | — | — | 2.0 | 2.0 | — | — |
| Nonionic surfactant[2] | — | — | 2.0 | 2.0 | — | — | 2.0 | 2.0 | — | — | 2.0 | 2.0 |
| Poly acrylic acid sodium salt[3] | 1.0 | 1.0 | 1.0 | 1.0 | 1.0 | 1.0 | 1.0 | 1.0 | 1.0 | 1.0 | 1.0 | 1.0 |
| Sodium lauroyloxy-benzenesulfonate | — | 4.0 | — | 4.0 | — | 4.0 | — | 4.0 | — | 4.0 | — | 4.0 |
| Protopectinase PB[4] | 0.1 | 0.1 | 0.1 | 0.1 | — | — | — | — | — | — | — | — |
| Protopectinase RB[5] | — | — | — | — | 0.1 | 0.1 | 0.1 | 0.1 | — | — | — | — |
| Detergency against mud-smudged cloth (%) | 73.7 | 75.3 | 73.6 | 74.8 | 73.8 | 75.2 | 73.8 | 74.8 | 62.2 | 63.1 | 62.0 | 62.8 |

[1] Linear alkylbenzenesulfonate-Na (Carbon number 12–14)
[2] Polyoxyethylene alkyl ether (carbon number of alkyl group = 12–14; Average mole number of E.O. added = 12)
[3] Average molecular weight: 8.000
[4] Protopectinase PB granulated by the method described in Japanese Patent Application Laid-Open (kokai) No. 62-257990. 50,000 U/g granule (pectinase activity at pH 10.0).
[5] Protopectinase RB granulated by the method described in Japanese Patent Application Laid-Open (kokai) No. 62-257990. 50,000 U/g granule (pectinase activity at pH 10.0).

From Table 10, it is understood that the protopectinase-containing bleach-detergent compositions of the present invention exhibit remarkable detergency against mud soil.

C. Effects Resulting from the Combined Use of Protopectinase and Cellulase and/or Protease:

A variety of enzymes shown in Table 10 were incorporated into the aforementioned detergent (a) in amounts as indicated in Table 11, and pieces of artificially smudged cloth were washed by use of the resultant detergent compositions (pH of the washing liquids: 10.7; washing conditions: Terg-O-Tometer 100 rpm, 10 minutes, 30° C.).

This synergistic effect attributable to the combined use of enzymes can also be obtained when other cellulases or proteases commercially available under the below-indicated trade names are used.

Cellulase: Celluzyme (manufactured by Novo Nordisk A/S)

Protease: Alkalase, Esperase, Savinase, Durazym (manufactured by Novo Nordisk A/S); Purafect, Maxapem, Properase (manufactured by Genencor Int. Inc.).

TABLE 11

|  | Formula 1 | Formula 2 | Formula 3 | Formula 4 | Formula 5 | Formula 6 | Formula 7 | Formula 8 | Formula 9 |
| --- | --- | --- | --- | --- | --- | --- | --- | --- | --- |
| Protopectinase PB[1] | — | 0.2% | 0.2% | 0.2% | 0.2% | — | — | — | — |
| Protopectinase RB[2] | — | 0.2% | 0.2% | 0.2% | 0.2% | 0.2% | 0.2% | 0.2% | 0.2% |
| Cellulase[3] | — | — | 0.7% | — | 0.7% | — | 0.7% | — | 0.7% |
| Protease[4] | — | — | — | 1.0% | 1.0% | — | — | 1.0% | 1.0% |
| Detergency against mud-smudged cloth (%) | 44.8 | 50.4 | 52.8 | 52.4 | 54.9 | 50.6 | 53.1 | 52.4 | 55.1 |

[1] Protopectinase PB granulated by the method described in Japanese Patent Application Laid-Open (kokai) No. 62-257990. 50,000 U/g granule (pectinase activity at pH 10.0).
[2] Protopectinase RB granulated by the method described in Japanese Patent Application Laid-Open (kokai) No. 62-257990. 50,000 U/g granule (pectinase activity at pH 10.0).
[3] KAC-500 (cellulase; manufactured by Kao Corporation). 500 U/g granule.
[4] Protease K-16 granulated by the method described in Japanese Patent Application Laid-Open (kokai) No. 62-257990. 5 U/g granule.

From the above results, it is understood that when the protopectinases of the present invention are used in combination with cellulase or protease, more enhanced detergency effect can be obtained. Moreover, when the protopectinases of the present invention are used in combination with cellulase and protease so as to make a three-component system, even more improved detergency effect against muddy soil is obtained.

INDUSTRIAL APPLICABILITY

As described above, the detergent compositions of the present invention have very high detergency against mud soil, and thus are particularly useful for washing clothes.

This application claims priorities based on Japanese patent application Nos. 9-091142 and 9-242736, filed on Apr. 9, 1997 and Sep. 8, 1997, respectively, which are incorporated herein by reference.

What is claimed is:

1. A detergent composition comprising protopectinase having an optimum pH for the reaciton of 7.0 or higher when protopectin or polygalacturonic acid is used as a substrate, and a surfactant.

2. The detergent composition as claimed in claim 1, wherein the protopectinase has an ability of releasing cotton pectin in an amount of not less than 0.2 mg/g cotton.

3. The detergent composition as claimed in claim 1, wherein the protopectinase is derived from a microorganism which belongs to the genus Bacillus.

4. The detergent composition as claimed in claim 1, wherein the protopectinase has pectic acid lyase activity.

5. The detergent composition as claimed in claim 1, further comprising a cellulase.

6. The detergent composition as claimed in claim 1, further comprising a protease.

7. The detergent composition as claimed in claim 1, further comprising a bleaching agent.

8. The detergent composition as claimed in claim 2, wherein the protopectinase is derived from a microorganism which belongs to the genus Bacillus.

9. The detergent composition as claimed in claim 2, wherein the protopectinase has pectic acid lyase activity.

10. The detergent composition as claimed in claim 3, wherein the protopectinase has pectic acid lyase activity.

11. The detergent composition as claimed in claim 2, further comprising a cellulase.

12. The detergent composition as claimed in claim 3, further comprising a cellulase.

13. The detergent composition as claimed in claim 4, further comprising a cellulase.

14. The detergent composition as claimed in claim 2, further comprising a protease.

15. The detergent composition as claimed in claim 3, further comprising a protease.

16. The detergent composition as claimed in claim 4, further comprising a protease.

17. The detergent composition as claimed in claim 6, further comprising a protease.

18. The detergent composition as claimed in claim 2, further comprising a bleaching agent.

19. The detergent composition as claimed in claim 3, further comprising a bleaching agent.

20. The detergent composition as claimed in claim 4, further comprising a bleaching agent.

21. The detergent composition as claimed in claim 5, further comprising a bleaching agent.

22. The detergent composition as claimed in claim 6, further comprising a bleaching agent.

23. The detergent composition as claimed in claim 1, wherein the optimum pH for the reaction is 7.5 or higher.

* * * * *

UNITED STATES PATENT AND TRADEMARK OFFICE
CERTIFICATE OF CORRECTION

PATENT NO. : 6,172,030 B1
DATED : January 9, 2001
INVENTOR(S): Yasunao, Wada et al.

It is certified that error appears in the above-identified patent and that said Letters Patent is hereby corrected as shown below:

ON THE TITLE PAGE

Item (22) PCT Filed:

change "April 9, 1998"

to --April 8, 1998--

Column 1; Line 5;

change "April 9, 1997"

to --April 8, 1998--

Signed and Sealed this

Twenty-ninth Day of May, 2001

Attest:

NICHOLAS P. GODICI

Attesting Officer      Acting Director of the United States Patent and Trademark Office

SEQUENCE LISTING

<160> NUMBER OF SEQ ID NOS: 14

<210> SEQ ID NO 1
<211> LENGTH: 591
<212> TYPE: DNA
<213> ORGANISM: Bacillus sp.
<220> FEATURE:
<223> OTHER INFORMATION: Strain: KSM-P15
<221> NAME/KEY: CDS
<222> LOCATION: (1)..(591)

<400> SEQUENCE: 1

```
gcg ccg acg gtc gtt cat gaa acg att cgt gtg cct gcc ggt cag acg        48
Ala Pro Thr Val Val His Glu Thr Ile Arg Val Pro Ala Gly Gln Thr
 1               5                  10                  15 ttt gac gga aaa ggg cag acc tat gtg gct aat ccg aat aca ttg ggg        96
Phe Asp Gly Lys Gly Gln Thr Tyr Val Ala Asn Pro Asn Thr Leu Gly
             20                  25                  30 gac gga tcg cag gcg gag aat cag aag ccg atc ttt cgt ctg gag gct       144
Asp Gly Ser Gln Ala Glu Asn Gln Lys Pro Ile Phe Arg Leu Glu Ala
         35                  40                  45 ggg gca agc ctg aaa aat gta gtg att ggc gct cct gcc gct gac ggg       192
Gly Ala Ser Leu Lys Asn Val Val Ile Gly Ala Pro Ala Ala Asp Gly
     50                  55                  60 gtg cac tgc tac ggg gat tgt acg att aca aat gtc atc tgg gag gat       240
Val His Cys Tyr Gly Asp Cys Thr Ile Thr Asn Val Ile Trp Glu Asp
 65                  70                  75                  80 gtt ggt gag gat gcg ctg acg ctt aaa tcg tcc gga acg gtg aac atc       288
Val Gly Glu Asp Ala Leu Thr Leu Lys Ser Ser Gly Thr Val Asn Ile
                 85                  90                  95 tcg ggc ggg gca gcc tac aag gcg tat gac aag gtg ttc caa atc aat       336
Ser Gly Gly Ala Ala Tyr Lys Ala Tyr Asp Lys Val Phe Gln Ile Asn
            100                 105                 110 gca gcg ggg acg atc aac att cgt aac ttc agg gcc gat gac atc ggg       384
Ala Ala Gly Thr Ile Asn Ile Arg Asn Phe Arg Ala Asp Asp Ile Gly
        115                 120                 125 aag ctg gtt cgg cag aac gga ggc acc acc tac aaa gtg gtg atg aac       432
Lys Leu Val Arg Gln Asn Gly Gly Thr Thr Tyr Lys Val Val Met Asn
    130                 135                 140 gtg gaa aac tgc aac att tcc aga gtg aag gat gcg atc ctg aga acg       480
Val Glu Asn Cys Asn Ile Ser Arg Val Lys Asp Ala Ile Leu Arg Thr
145                 150                 155                 160 gac agc agc aca agc aca gga cga att gtg aat acc cgc tat tct aac       528
Asp Ser Ser Thr Ser Thr Gly Arg Ile Val Asn Thr Arg Tyr Ser Asn
                165                 170                 175 gtg cca aca ttg ttc aaa ggc ttt aaa tca ggc aat acc acc gca tcc       576
Val Pro Thr Leu Phe Lys Gly Phe Lys Ser Gly Asn Thr Thr Ala Ser
            180                 185                 190 gga aat acg cag tat                                                   591
Gly Asn Thr Gln Tyr
        195
```

<210> SEQ ID NO 2
<211> LENGTH: 197
<212> TYPE: PRT
<213> ORGANISM: Bacillus sp.
<223> OTHER INFORMATION: Strain: KSM-P15

<400> SEQUENCE: 2

```
Ala Pro Thr Val Val His Glu Thr Ile Arg Val Pro Ala Gly Gln Thr
 1               5                  10                  15
```

-continued

```
Phe Asp Gly Lys Gly Gln Thr Tyr Val Ala Asn Pro Asn Thr Leu Gly
            20                  25                  30

Asp Gly Ser Gln Ala Glu Asn Gln Lys Pro Ile Phe Arg Leu Glu Ala
        35                  40                  45

Gly Ala Ser Leu Lys Asn Val Val Ile Gly Ala Pro Ala Asp Gly
    50                  55                  60

Val His Cys Tyr Gly Asp Cys Thr Ile Thr Asn Val Ile Trp Glu Asp
 65                  70                  75                  80

Val Gly Glu Asp Ala Leu Thr Leu Lys Ser Ser Gly Thr Val Asn Ile
                85                  90                  95

Ser Gly Gly Ala Ala Tyr Lys Ala Tyr Asp Lys Val Phe Gln Ile Asn
                100                 105                 110

Ala Ala Gly Thr Ile Asn Ile Arg Asn Phe Arg Ala Asp Asp Ile Gly
            115                 120                 125

Lys Leu Val Arg Gln Asn Gly Gly Thr Thr Tyr Lys Val Val Met Asn
        130                 135                 140

Val Glu Asn Cys Asn Ile Ser Arg Val Lys Asp Ala Ile Leu Arg Thr
145                 150                 155                 160

Asp Ser Ser Thr Ser Thr Gly Arg Ile Val Asn Thr Arg Tyr Ser Asn
                165                 170                 175

Val Pro Thr Leu Phe Lys Gly Phe Lys Ser Gly Asn Thr Thr Ala Ser
                180                 185                 190

Gly Asn Thr Gln Tyr
            195

<210> SEQ ID NO 3
<211> LENGTH: 20
<212> TYPE: PRT
<213> ORGANISM: Bacillus sp.

<400> SEQUENCE: 3

Ala Pro Thr Val Val His Glu Thr Ile Arg Val Pro Ala Gly Gln Thr
 1               5                  10                  15

Phe Asp Gly Lys
            20

<210> SEQ ID NO 4
<211> LENGTH: 12
<212> TYPE: PRT
<213> ORGANISM: Bacillus sp.

<400> SEQUENCE: 4

Val Val Ile Gly Ala Pro Ala Ala Asp Gly Val His
 1               5                  10

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:primer 1
<223> OTHER INFORMATION: any n = g, c, a, or t

<400> SEQUENCE: 5
gcnccnacng tngtncayga racnat                                          26

<210> SEQ ID NO 6
<211> LENGTH: 9
<212> TYPE: PRT
```

```
<213> ORGANISM: Artificial Sequence
<220> FEATURE:
<223> OTHER INFORMATION: Description of Artificial Sequence:peptide from
      pectic acid lyase

<400> SEQUENCE: 6

Ala Pro Thr Val Val His Glu Thr Ile
  1               5

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:primer 2
<223> OTHER INFORMATION: any n = g, c, a, or t

<400> SEQUENCE: 7
cancantadc cncgnggncg ncg                                                23

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:lysyl
      endopeptidase-treated fragment

<400> SEQUENCE: 8

Val Val Ile Gly Ala Pro Ala Ala
  1               5

<210> SEQ ID NO 9
<211> LENGTH: 185
<212> TYPE: DNA
<213> ORGANISM: Artificial Sequence
<220> FEATURE:
<223> OTHER INFORMATION: Description of Artificial Sequence:primer

<400> SEQUENCE: 9
gcgcccactg tcgtgcacga aacgattcgt gtgcctgccg gtcagacgtt tgacggaaaa        60
gggcagacct atgtggctaa tccgaataca ttgggggacg gatcgcaggc ggagaatcag       120
aagccgatct ttcgtctgga ggctgggggca agcctgaaaa atgtagttat cggtgcaccg       180
gctgc                                                                  185

<210> SEQ ID NO 10
<211> LENGTH: 62
<212> TYPE: PRT
<213> ORGANISM: Artificial Sequence
<220> FEATURE:
<223> OTHER INFORMATION: Description of Artificial Sequence:peptide from
      primer

<400> SEQUENCE: 10

Ala Pro Thr Val Val His Glu Thr Ile Arg Val Pro Ala Gly Gln Thr
  1               5                  10                  15

Phe Asp Gly Lys Gly Gln Thr Tyr Val Ala Asn Pro Asn Thr Leu Gly
             20                  25                  30

Asp Gly Ser Gln Ala Glu Asn Gln Lys Pro Ile Phe Arg Leu Glu Ala
         35                  40                  45

Gly Ala Ser Leu Lys Asn Val Val Ile Gly Ala Pro Ala Ala
     50                  55                  60
```

```
<210> SEQ ID NO 11
<211> LENGTH: 185
<212> TYPE: DNA
<213> ORGANISM: Artificial Sequence
<220> FEATURE:
<223> OTHER INFORMATION: Description of Artificial Sequence:primer

<400> SEQUENCE: 11
cgtcggccac gtggctattg atgtaaaaag tccgaacggg gtcggaggtc tgctttctag      60
ccgaagacta agaggcggac gctaggcagg gggttacata agcctaatcg gtgtatccag     120
acgggaaaag gcagtttgca gactggccgt ccgtgtgctt agcaaagcac gtgctgtcac     180
ccgcg                                                                 185

<210> SEQ ID NO 12
<211> LENGTH: 62
<212> TYPE: PRT
<213> ORGANISM: Artificial Sequence
<220> FEATURE:
<223> OTHER INFORMATION: Description of Artificial Sequence:peptide from
      primer

<400> SEQUENCE: 12

Ala Ala Pro Ala Gly Ile Val Val Asn Lys Leu Ser Ala Gly Ala Glu
  1               5                  10                  15

Leu Arg Phe Ile Pro Lys Gln Asn Glu Ala Gln Ser Gly Asp Gly Leu
             20                  25                  30

Thr Asn Pro Asn Ala Val Tyr Thr Gln Gly Lys Gly Asp Phe Thr Gln
         35                  40                  45

Gly Ala Pro Val Arg Ile Thr Glu His Val Val Thr Pro Ala
     50                  55                  60

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence:primer 5

<400> SEQUENCE: 13
gcgtcgactc gcggaggcgg cgccgacggt tgttc                                 35

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:primer 6

<400> SEQUENCE: 14
gtgtatatca aggagaagac cggcatg                                          27
```